(12) United States Patent
Niu et al.

(10) Patent No.: US 7,560,612 B2
(45) Date of Patent: Jul. 14, 2009

(54) EARLY-INFLORESCENCE-PREFERRED REGULATORY ELEMENTS AND USES THEREOF

(75) Inventors: Xiping Niu, Johnston, IA (US); Nicholas Bate, Urbandale, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 73 days.

(21) Appl. No.: 11/527,087

(22) Filed: Sep. 26, 2006

(65) Prior Publication Data

US 2007/0136891 A1 Jun. 14, 2007

Related U.S. Application Data

(63) Continuation-in-part of application No. 10/387,937, filed on Mar. 13, 2003, now abandoned.

(60) Provisional application No. 60/364,065, filed on Mar. 13, 2002.

(51) Int. Cl.
C12N 15/82 (2006.01)
A01H 5/00 (2006.01)
A01H 5/10 (2006.01)

(52) U.S. Cl. .................. 800/287; 800/298; 800/320; 800/320.1; 800/320.2; 800/320.3; 536/24.1; 435/320.1; 435/419; 435/468

(58) Field of Classification Search .................. None
See application file for complete search history.

(56) References Cited

U.S. PATENT DOCUMENTS 6,002,069 A 12/1999 Yanofsky
6,025,483 A 2/2000 Yanofsky
6,355,863 B1 3/2002 Yanofsky

FOREIGN PATENT DOCUMENTS

WO 0023578 4/2000
WO 03/007861 3/2003

OTHER PUBLICATIONS

Kim Y. et al. A 20 nucleotide upstream element is essential for the nopaline synthase (nos) promoter activity. Plant Mol Biol. Jan. 1994;24(1):105-17.*
de Pater S. et al. A 22-bp fragment of the pea lectin promoter containing essential TGAC-like motifs confers seed-specific gene expression. Plant Cell. Aug. 1993;5(8):877-86.*
Becker D. et al. Fertile transgenic wheat from microprojectile bombardment of scutellar tissue. Plant J. Feb. 1994;5(2):299-307.*
Krizek BA and Riechmann, JL; "Use of the APETALA1 promoter to assay the in vitro function of chimeric MADS box genes"; Sex Plant Reprod. (1999) 12:14-26.
Chen, L, et al.; "EMF Genes Regulate Arabidopsis Inflorescence Development"; The Plant Cell (1997) 9:2011-2024.
Gocal, GFW, et al.; "Evolution of Floral Meristem Identity Genes. Analysis of *Lolium temulentum* Genes Related to APELALA1 and LEAFY of Arabidopsis"; Plant Physiology (2001) 125.
Munster, I, et al.; "Maize Mads-Box Genes Galore"; Maydica (2002) 47:287-301.

* cited by examiner

*Primary Examiner*—Cynthia Collins
(74) *Attorney, Agent, or Firm*—Pioneer Hi-Bred Int'l., Inc.

(57) ABSTRACT

The present invention provides compositions and methods for regulating expression of isolated nucleotide sequences in a plant. The compositions are novel nucleic acid sequences for regulatory elements providing expression preferentially in the inflorescence meristem and developing floral tissues. Methods for expressing an isolated nucleotide sequence in a plant using the regulatory sequences are also provided, as well as expression constructs, vectors, and transformed cells and plants.

17 Claims, 16 Drawing Sheets

```
  1 AGCGCCCAAT ACGCAAACCG CCTCTCCCCG CGCGTTGGCC GATTCATTAA
    TCGCGGGTTA TGCGTTTGGC GGAGAGGGGC GCGCAACCGG CTAAGTAATT
 51 TGCAGCTGGC ACGACAGGTT TCCCGACTGG AAAGCGGGCA GTGAGCGCAA
    ACGTCGACCG TGCTGTCCAA AGGGCTGACC TTTCGCCCGT CACTCGCGTT
101 CGCAATTAAT GTGAGTTAGC TCACTCATTA GGCACCCCAG GCTTTACACT
    GCGTTAATTA CACTCAATCG AGTGAGTAAT CCGTGGGGTC CGAAATGTGA
151 TTATGCTTCC GGCTCGTATG TTGTGTGGAA TTGTGAGCGG ATAACAATTT
    AATACGAAGG CCGAGCATAC AACACACCTT AACACTCGCC TATTGTTAAA
                                                       HindIII
                                                       ~~~~~~~
201 CACACAGGAA ACAGCTATGA CCATGATTAC GCCAAGCTTG GTACCGAGCT
    GTGTGTCCTT TGTCGATACT GGTACTAATG CGGTTCGAAC CATGGCTCGA
         BamHI                              GenomeWalker cloning adapt
         ~~~~~~~                            ~~~~~~~~~~~~~~~~~~~~~~~~
                                  EcoRI
                                  ~~~~~
251 CGGATCCACT AGTAACGGCC GCCAGTGTGC TGGAATTCGC CCTTACTATA
    GCCTAGGTGA TCATTGCCGG CGGTCACACG ACCTTAAGCG GGAATGATAT
         GenomeWalker cloning adapter
         ~~~~~~~~~~~~~~~~~~~~~~~~~~~~
                              XmaI
                              ~~~~~~~
                    SalI      SmaI
                    ~~~~~     ~~~~~
301 GGGCACGCGT GGTCGACGGC CCGGGCTGGT CCTTTTTCTT TTTCTCCACA
    CCCGTGCGCA CCAGCTGCCG GGCCCGACCA GGAAAAAGAA AAAGAGGTGT
351 ACATGAACCT TACTAGAACA CTGCCCCACT TAAAAGAATG AGGGTAGAAC
    TGTACTTGGA ATGATCTTGT GACGGGGTGA ATTTTCTTAC TCCCATCTTG
401 TCTTGAATCT TAGGGATTTG AACTCCTTGC AGTACCTCAT AACAAGGGTG
    AGAACTTAGA ATCCCTAAAC TTGAGGAACG TCATGGAGTA TTGTTCCCAC
451 TTACATGTCC TTCTTCTGCT GTTGCTGCTT GAGCAGGATA TAGAGAGATG
    AATGTACAGG AAGAAGACGA CAACGACGAA CTCGTCCTAT ATCTCTCTAC
501 ACCGACACCG GGTTGATCTT GGGACAACCT TCTTCTCATC TTTTCTTCGT
    TGGCTGTGGC CCAACTAGAA CCCTGTTGGA AGAAGAGTAG AAAAGAAGCA
551 TGTTTTCTTT TCTATTCTCA CTACCTTTTT CTTTCTCTTT GTTCTTCCCA
    ACAAAAGAAA AGATAAGAGT GATGGAAAAA GAAAGAGAAA CAAGAAGGGT
601 CTGGAGGATT CTATCAAAAA GTATTACCAT CATACAGGAG AGGAACCCGA
    GACCTCCTAA GATAGTTTTT CATAATGGTA GTATGTCTCC TCCTTGGGCT
651 AGACTATGAA CCATGTACAA CAGTCTTCAA CCCAAGAATC ACCAAGCATT
    TCTGATACTT GGTACATGTT GTCAGAAGTT GGGTTCTTAG TGGTTCGTAA
701 GTGATCTTAG GGGCGAGGGA GTGGAAAATG GAGTTGCTTG TGATTTGGCA
    CACTAGAATC CCCGCTCCCT CACCTTTTAC CTCAACGAAC ACTAAACCGT
751 GAGGGAATTT TATCAGGAGT GTTTTGCTTT GAGTGGAATG GGAACTGAGG
    CTCCCTTAAA ATAGTCCTCA CAAAACGAAA CTCACCTTAC CCTTGACTCC
801 GAGTTGTTGG GGGGGGGGGG TTTATAGGCG AGTGGGAGTG CTCGGGTGCG
    CTCAACAACC CCCCCCCCCC AAATATCCGC TCACCCTCAC GAGCCCACGC
851 GAGTGTGGTG ATGGAACAGG TGACATGAGG TAGCAGGTCG ATGGAGGGGG
    CTCACACCAC TACCTTGTCC ACTGTACTCC ATCGTCCAGC TACCTCCCCC
901 GCTGTTGCCG GCGATGATGG CGGCGGTGGG TGCGCTGCAA AGGAGGGCGT
    CGACAACGGC CGCTACTACC GCCGCCACCC ACGCGACGTT TCCTCCCGCA
951 GGGGCGGTGG TAGTGCGCAT GGAGGCGGGC ACGCGTGCGG GGGCACAAG
    CCCCGCCACC ATCACGCGTA CCTCCGCCCG TGCGCACGCC CCCCGTGTTC
```

FIGURE 3A

```
1001  TGAGTGGTGG GGTCGATGAC CCTGATGTTT GTGGTCTCTG GTTCCAAGAA
      ACTCACCACC CCAGCTACTG GGACTACAAA CACCAGAGAC CAAGGTTCTT
1051  TCTTTGTCTC TCTTTATGAT AATAACTTCT TTTGTCGTCC TTTTCTGTTT
      AGAAACAGAG AGAAATACTA TTATTGAAGA AAACAGCAGG AAAAGACAAA
1101  ACTTTGACTC AGGGGCAGTG CTTTGATTCT CACGGTCGGT CCTTTTGACT
      TGAAACTGAG TCCCCGTCAC GAAACTAAGA GTGCCAGCCA GGAAAACTGA
1151  GAGTGACTGG ACATGTTTCT TCTGTAGCAT TGTACAACAT GTACTTTGTG
      CTCACTGACC TGTACAAAGA AGACATCGTA ACATGTTGTA CATGAAACAC
1201  CAAGCTACAA GGCCACATTT TTTGAAGCAT AGATTCTTTC CCCCAAACAA
      GTTCGATGTT CCGGTGTAAA AAACTTCGTA TCTAAGAAAG GGGGTTTGTT
1251  TTTATACAAA TATGCAAGGC TACACTTCTT GTATTTCTAT AACATTGTAC
      AAATATGTTT ATACGTTCCG ATGTGAAGAA CATAAAGATA TTGTAACATG
                                    HindIII
1301  ATTCATGACA GAGGCTCAAA AGCTTGTAAA TTTTGTGCAG GTTTAATTCA
      TAAGTACTGT CTCCGAGTTT TCGAACATTT AAAACACGTC CAAATTAAGT
1351  TGTAAAGTTC CCTTGTAGAG TCATGACAAC ATCGTACTAT AAAATTATTC
      ACATTTCAAG GGAACATCTC AGTACTGTTG TAGCATGATA TTTTAATAAG
1401  TACAAAAACC ACACATGACC CCCATGTTAT TTGGTGACAA TACAGAAACC
      ATGTTTTTGG TGTGTACTGG GGGTACAATA AACCACTGTT ATGTCTTTGG
1451  ACACATCTAG TGATGATATA ACACTGTACA GAAGCCACAA ATTATAATAT
      TGTGTAGATC ACTACTATAT TGTGACATGT CTTCGGTGTT TAATATTATA
                                                      BstEII
1501  ATAAAACACT ATACAAAGTA TCCAAATAAA GCCTAATAGG TATGGAGGGT
      TATTTTGTGA TATGTTTCAT AGGTTTATTT CGGATTATCC ATACCTCCCA
      BstEII
1551  AACCTGAATC TTTCCTAATA ATAATGAATA ATCTACAATA ATGATTTGTT
      TTGGACTTAG AAAGGATTAT TATTACTTAT TAGATGTTAT TACTAAACAA
1601  TGGACAAAGA GAATTAAACG GTATTGAGTG GGCTAAAATT CCTTGTTATT
      ACCTGTTTCT CTTAATTTGC CATAACTCAC CCGATTTTAA GGAACAATAA
1651  CAAAACCCTC AATCACAGTT TCTCCGAGGG AAAAAGAAAC AGGGGAGGAC
      GTTTTGGGAG TTAGTGTCAA AGAGGCTCCC TTTTTCTTTG TCCCCTCCTG
1701  ACTCAGGCTG TTCACAATAG GGATTTCATA TCGCTCTTTC CAACAATGCC
      TGAGTCCGAC AAGTGTTATC CCTAAAGTAT AGCGAGAAAG GTTGTTACGG
1751  ACATCATCAA AAGTGTTATG AAACTAAAAA TGAAATAATA CTTCTCAATG
      TGTAGTAGTT TTCACAATAC TTTGATTTTT ACTTTATTAT GAAGAGTTAC
1801  CAAACTTTCA TTTTCATAGA TTAATATACT AATTAAATGA TGCAACTAAA
      GTTTGAAAGT AAAAGTATCT AATTATATGA TTAATTACT ACGTTGATTT
1851  TAACCAATAG ATGTTAGTAA AATATGGTAA GATTAAACAA ACCACTATCA
      ATTGGTTATC TACAATCATT TTATACCATT CTAATTGTT TGGTGATAGT
1901  ATGGACATTT CACATAGTTT CCAAGACTTT GAAAACGGGT TGACATGATT
      TACCTGTAAA GTGTATCAAA GGTTCTGAAA CTTTTGCCCA ACTGTACTAA
1951  TCATCCACAT CAAACTAATT TTATCTCTGA AACCCATTCA TTTTAAATGA
      AGTAGGTGTA GTTTGATTAA AATAGAGACT TTGGGTAAGT AAAATTTACT
2001  TATGGCATAA CGTCCAAAAT GCTGACGTGA CATACCATTA AATGTGCATG
      ATACCGTATT GCAGGTTTTA CGACTGCACT GTATGGTAAT TTACACGTAC
```

FIGURE 3B

```
2051  AAACTCCCAT AAAACTTTTA TTGATAATAG CCTCACAGAC ATCCGGTCCT
      TTTGAGGGTA TTTTGAAAAT AACTATTATC GGAGTGTCTG TAGGCCAGGA
                                        Pstl
                                      wwwwwww
2101  ACACCCGTGT GGACCCATCA GCCAGACGCC CTGCAGCAAA CGCGACGTTT
      TGTGGGCACA CCTGGGTAGT CGGTCTGCGG GACGTCGTTT GCGCTGCAAA 2151  GACTTGCCAT CTCGCTCCCT TGTGCCCGAC CGACCCTGGA AGGCTGGACT
      CTGAACGGTA GAGCGAGGGA ACACGGGCTG GCTGGGACCT TCCGACCTGA 2201  GGAACTGGAA CAAGCAAAAT GGAAAAAACC ATATCTCACC ACTGAACCGC
      CCTTGACCTT GTTCGTTTTA CCTTTTTTGG TATAGAGTGG TGACTTGGCG 2251  ACCCTTCCGG CCCACGCCAG GCTCGACCAA TCCCTGCCCC GCGCGCCCTG
      TGGGAAGGCC GGGTGCGGTC CGAGCTGGTT AGGGACGGGG CGCGCGGGAC 2301  ACGAGCGCAT CACTCGAACG CCGGCCTCGC TAGGCCCATC CTTCTGGCCC
      TGCTCGCGTA GTGAGCTTGC GGCCGGAGCG ATCCGGGTAG GAAGACCGGG 2351  GCAATAACGA TCCCCGTCAT GATCCGACGG TCTAGCTGCC TCCACGCCGC
      CGTTATTGCT AGGGGCAGTA CTAGGCTGCC AGATCGACGG AGGTGCGGCG 2401  TCCAAAACCC CCGCGTCCAA TCAAAACACG ACAGCGGGAC GAGCGAAACC
      AGGTTTTGGG GGCGCAGGTT AGTTTTGTGC TGTCGCCCTG CTCGCTTTGG 2451  ACCGTGGTTT CGCCAAACCG CTTTCCTTCC CATCTAAAAC CGCCCCCTCC
      TGGCACCAAA GCGGTTTGGC GAAAGGAAGG GTAGATTTTG GCGGGGGAGG
                                    p0092.chwaj31r & p0004.cb1hd54r
                                      ▼
                                      Xhol            Xhol
                                    wwwwwwww          wwww
2501  CTTCCTCTTC TCCTAGCTCT CTTGCCTGCG CACCACTCGA GTCGAGACTC
      GAAGGAGAAG AGGATCGAGA GAACGGACGC GTGGTGAGCT CAGCTCTGAG
                     cloning site   EcoRI
                       wwww       wwwwwwww
      Xhol                                Pstl
      wwww                              wwwwwwww
2551  GAGAGGCACC TGATCTTTCA AGGGCGAATT CTGCAGATAT CCATCACACT
      CTCTCCGTGG ACTAGAAAGT TCCCGCTTAA GACGTCTATA GGTAGTGTGA
          Notl
        wwwwwwwwww
                Xhol         Xbal
               wwwwwww     wwwwwwww
2601  GGCGGCCGCT CGAGCATGCA TCTAGAGGGC CCAATTCGCC CTATAGTGAG
      CCGCCGGCGA GCTCGTACGT AGATCTCCCG GGTTAAGCGG GATATCACTC 2651  TCGTATTACA ATTCACTGGC CGTCGTTTTA CAACGTCGTG ACTGGGAAAA
      AGCATAATGT TAAGTGACCG GCAGCAAAAT GTTGCAGCAC TGACCCTTTT 2701  CCCTGGCGTT ACCCAACTTA ATCGCCTTGC AGCACATCCC CCTTTCGCCA
      GGGACCGCAA TGGGTTGAAT TAGCGGAACG TCGTGTAGGG GGAAAGCGGT 2751  GCTGGCGTAA TAGCGAAGAG GCCCGCACCG ATCGCCCTTC CCAACAGTTG
      CGACCGCATT ATCGCTTCTC CGGGCGTGGC TAGCGGGAAG GGTTGTCAAC 2801  CGCAGCCTGA ATGGCGAATG GGACGCGCCC TGTAGCGGCG CATTAAGCGC
      GCGTCGGACT TACCGCTTAC CCTGCGCGGG ACATCGCCGC GTAATTCGCG 2851  GGCGGGTGTG GTGGTTACGC GCAGCGTGAC CGCTACACTT GCCAGCGCCC
      CCGCCCACAC CACCAATGCG CGTCGCACTG GCGATGTGAA CGGTCGCGGG 2901  TAGCGCCCGC TCCTTTCGCT TTCTTCCCTT CCTTTCTCGC CACGTTCGCC
      ATCGCGGGCG AGGAAAGCGA AAGAAGGGAA GGAAAGAGCG GTGCAAGCGG 2951  GGCTTTCCCC GTCAAGCTCT AAATCGGGGG CTCCCTTTAG GGTTCCGATT
      CCGAAAGGGG CAGTTCGAGA TTTAGCCCCC GAGGGAAATC CCAAGGCTAA 3001  TAGAGCTTTA CGGCACCTCG ACCGCAAAAA ACTTGATTTG GGTGATGGTT
      ATCTCGAAAT GCCGTGGAGC TGGCGTTTTT TGAACTAAAC CCACTACCAA
```

FIGURE 3C

```
3051  CACGTAGTGG GCCATCGCCC TGATAGACGG TTTTTCGCCC TTTGACGTTG
      GTGCATCACC CGGTAGCGGG ACTATCTGCC AAAAAGCGGG AAACTGCAAC
3101  GAGTCCACGT TCTTTAATAG TGGACTCTTG TTCCAAACTG GAACAACACT
      CTCAGGTGCA AGAAATTATC ACCTGAGAAC AAGGTTTGAC CTTGTTGTGA
3151  CAACCCTATC GCGGTCTATT CTTTTGATTT ATAAGGGATT TTGCCGATTT
      GTTGGGATAG CGCCAGATAA GAAAACTAAA TATTCCCTAA AACGGCTAAA
3201  CGGCCTATTG GTTAAAAAAT GAGCTGATTT AACAAATTCA GGGCGCAAGG
      GCCGGATAAC CAATTTTTTA CTCGACTAAA TTGTTTAAGT CCCGCGTTCC
3251  GCTGCTAAAG GAACCGGAAC ACGTAGAAAG CCAGTCCGCA GAAACGGTGC
      CGACGATTTC CTTGGCCTTG TGCATCTTTC GGTCAGGCGT CTTTGCCACG
3301  TGACCCCGGA TGAATGTCAG CTACTGGGCT ATCTGGACAA GGGAAAACGC
      ACTGGGGCCT ACTTACAGTC GATGACCCGA TAGACCTGTT CCCTTTTGCG
3351  AAGCGCAAAG AGAAAGCAGG TAGCTTGCAG TGGGCTTACA TGGCGATAGC
      TTCGCGTTTC TCTTTCGTCC ATCGAACGTC ACCCGAATGT ACCGCTATCG
3401  TAGACTGGGC GGTTTTATGG ACAGCAAGCG AACCGGAATT GCCAGCTGGG
      ATCTGACCCG CCAAAATACC TGTCGTTCGC TTGGCCTTAA CGGTCGACCC
3451  GCGCCCTCTG GTAAGGTTGG GAAGCCCTGC AAAGTAAACT GGATGGCTTT
      CGCGGGAGAC CATTCCAACC CTTCGGGACG TTTCATTTGA CCTACCGAAA
3501  CTTGCCGCCA AGGATCTGAT GGCGCAGGGG ATCAAGATCT GATCAAGAGA
      GAACGGCGGT TCCTAGACTA CCGCGTCCCC TAGTTCTAGA CTAGTTCTCT
3551  CAGGATGAGG ATCGTTTCGC ATGATTGAAC AAGATGGATT GCACGCAGGT
      GTCCTACTCC TAGCAAAGCG TACTAACTTG TTCTACCTAA CGTGCGTCCA
3601  TCTCCGGCCG CTTGGGTGGA GAGGCTATTC GGCTATGACT GGGCACAACA
      AGAGGCCGGC GAACCCACCT CTCCGATAAG CCGATACTGA CCCGTGTTGT
3651  GACAATCGGC TGCTCTGATG CCGCCGTGTT CCGGCTGTCA GCGCAGGGGC
      CTGTTAGCCG ACGAGACTAC GGCGGCACAA GGCCGACAGT CGCGTCCCCG
                                                         PstI
3701  GCCCGGTTCT TTTTGTCAAG ACCGACCTGT CCGGTGCCCT GAATGAACTG
      CGGGCCAAGA AAAACAGTTC TGGCTGGACA GGCCACGGGA CTTACTTGAC
         PstI
3751  CAGGACGAGG CAGCGCGGCT ATCGTGGCTG GCCACGACGG GCGTTCCTTG
      GTCCTGCTCC GTCGCGCCGA TAGCACCGAC CGGTGCTGCC CGCAAGGAAC
3801  CGCAGCTGTG CTCGACGTTG TCACTGAAGC GGGAAGGGAC TGGCTGCTAT
      GCGTCGACAC GAGCTGCAAC AGTGACTTCG CCCTTCCCTG ACCGACGATA
3851  TGGGCGAAGT GCCGGGGCAG GATCTCCTGT CATCTCGCCT TGCTCCTGCC
      ACCCGCTTCA CGGCCCCGTC CTAGAGGACA GTAGAGCGGA ACGAGGACGG
3901  GAGAAAGTAT CCATCATGGC TGATGCAATG CGGCGGCTGC ATACGCTTGA
      CTCTTTCATA GGTAGTACCG ACTACGTTAC GCCGCCGACG TATGCGAACT
3951  TCCGGCTACC TGCCCATTCG ACCACCAAGC GAAACATCGC ATCGAGCGAG
      AGGCCGATGG ACGGGTAAGC TGGTGGTTCG CTTTGTAGCG TAGCTCGCTC
4001  CACGTACTCG GATGGAAGCC GGTCTTGTCG ATCAGGATGA TCTGGACGAA
      GTGCATGAGC CTACCTTCGG CCAGAACAGC TAGTCCTACT AGACCTGCTT
4051  GAGCATCAGG GGCTCGCGCC AGCCGAACTG TTCGCCAGGC TCAAGGCGCG
      CTCGTAGTCC CCGAGCGCGG TCGGCTTGAC AAGCGGTCCG AGTTCCGCGC
```

FIGURE 3D

```
                                                Ncol
4101    CATGCCCGAC GGCGAGGATC TCGTCGTGAT CCATGGCGAT GCCTGCTTGC
        GTACGGGCTG CCGCTCCTAG AGCAGCACTA GGTACCGCTA CGGACGAACG 4151    CGAATATCAT GGTGGAAAAT GGCCGCTTTT CTGGATTCAA CGACTGTGGC
        GCTTATAGTA CCACCTTTTA CCGGCGAAAA GACCTAAGTT GCTGACACCG 4201    CGGCTGGGTG TGGCGGACCG CTATCAGGAC ATAGCGTTGG ATACCCGTGA
        GCCGACCCAC ACCGCCTGGC GATAGTCCTG TATCGCAACC TATGGGCACT 4251    TATTGCTGAA GAGCTTGGCG GCGAATGGGC TGACCGCTTC CTCGTGCTTT
        ATAACGACTT CTCGAACCGC CGCTTACCCG ACTGGCGAAG GAGCACGAAA 4301    ACGGTATCGC CGCTCCCGAT TCGCAGCGCA TCGCCTTCTA TCGCCTTCTT
        TGCCATAGCG GCGAGGGCTA AGCGTCGCGT AGCGGAAGAT AGCGGAAGAA 4351    GACGAGTTCT TCTGAATTGA AAAAGGAAGA GTATGAGTAT TCAACATTTC
        CTGCTCAAGA AGACTTAACT TTTTCCTTCT CATACTCATA AGTTGTAAAG 4401    CGTGTCGCCC TTATTCCCTT TTTTGCGGCA TTTTGCCTTC CTGTTTTTGC
        GCACAGCGGG AATAAGGGAA AAAACGCCGT AAAACGGAAG GACAAAAACG 4451    TCACCCAGAA ACGCTGGTGA AAGTAAAAGA TGCTGAAGAT CAGTTGGGTG
        AGTGGGTCTT TGCGACCACT TTCATTTTCT ACGACTTCTA GTCAACCCAC 4501    CACGAGTGGG TTACATCGAA CTGGATCTCA ACAGCGGTAA GATCCTTGAG
        GTGCTCACCC AATGTAGCTT GACCTAGAGT TGTCGCCATT CTAGGAACTC 4551    AGTTTTCGCC CCGAAGAACG TTTTCCAATG ATGAGCACTT TTAAAGTTCT
        TCAAAAGCGG GGCTTCTTGC AAAAGGTTAC TACTCGTGAA AATTTCAAGA 4601    GCTATGTCAT ACACTATTAT CCCGTATTGA CGCCGGGCAA GAGCAACTCG
        CGATACAGTA TGTGATAATA GGGCATAACT GCGGCCCGTT CTCGTTGAGC 4651    GTCGCCGGGC GCGGTATTCT CAGAATGACT TGGTTGAGTA CTCACCAGTC
        CAGCGGCCCG CGCCATAAGA GTCTTACTGA ACCAACTCAT GAGTGGTCAG 4701    ACAGAAAAGC ATCTTACGGA TGGCATGACA GTAAGAGAAT TATGCAGTGC
        TGTCTTTTCG TAGAATGCCT ACCGTACTGT CATTCTCTTA ATACGTCACG 4751    TGCCATAACC ATGAGTGATA ACACTGCGGC CAACTTACTT CTGACAACGA
        ACGGTATTGG TACTCACTAT TGTGACGCCG GTTGAATGAA GACTGTTGCT 4801    TCGGAGGACC GAAGGAGCTA ACCGCTTTTT TGCACAACAT GGGGGATCAT
        AGCCTCCTGG CTTCCTCGAT TGGCGAAAAA ACGTGTTGTA CCCCCTAGTA 4851    GTAACTCGCC TTGATCGTTG GGAACCGGAG CTGAATGAAG CCATACCAAA
        CATTGAGCGG AACTAGCAAC CCTTGGCCTC GACTTACTTC GGTATGGTTT 4901    CGACGAGAGT GACACCACGA TGCCTGTAGC AATGCCAACA ACGTTGCGCA
        GCTGCTCTCA CTGTGGTGCT ACGGACATCG TTACGGTTGT TGCAACGCGT 4951    AACTATTAAC TGGCGAACTA CTTACTCTAG CTTCCCGGCA ACAATTAATA
        TTGATAATTG ACCGCTTGAT GAATGAGATC GAAGGGCCGT TGTTAATTAT 5001    GACTGGATGG AGGCGGATAA AGTTGCAGGA CCACTTCTGC GCTCGGCCCT
        CTGACCTACC TCCGCCTATT TCAACGTCCT GGTGAAGACG CGAGCCGGGA 5051    TCCGGCTGGC TGGTTTATTG CTGATAAATC TGGAGCCGGT GAGCGTGGGT
        AGGCCGACCG ACCAAATAAC GACTATTTAG ACCTCGGCCA CTCGCACCCA 5101    CTCGCGGTAT CATTGCAGCA CTGGGGCCAG ATGGTAAGCC CTCCCGTATC
        GAGCGCCATA GTAACGTCGT GACCCCGGTC TACCATTCGG GAGGGCATAG 5151    GTAGTTATCT ACACGACGGG GAGTCAGGCA ACTATGGATG AACGAAATAG
        CATCAATAGA TGTGCTGCCC CTCAGTCCGT TGATACCTAC TTGCTTTATC
```

FIGURE 3E

```
5201  ACAGATCGCT GAGATAGGTG CCTCACTGAT TAAGCATTGG TAACTGTCAG
      TGTCTAGCGA CTCTATCCAC GGAGTGACTA ATTCGTAACC ATTGACAGTC
5251  ACCAAGTTTA CTCATATATA CTTTAGATTG ATTTAAAACT TCATTTTTAA
      TGGTTCAAAT GAGTATATAT GAAATCTAAC TAAATTTTGA AGTAAAAATT
5301  TTTAAAAGGA TCTAGGTGAA GATCCTTTTT GATAATCTCA TGACCAAAAT
      AAATTTTCCT AGATCCACTT CTAGGAAAAA CTATTAGAGT ACTGGTTTTA
5351  CCCTTAACGT GAGTTTTCGT TCCACTGAGC GTCAGACCCC GTAGAAAAGA
      GGGAATTGCA CTCAAAAGCA AGGTGACTCG CAGTCTGGGG CATCTTTTCT
5401  TCAAAGGATC TTCTTGAGAT CCTTTTTTTC TGCGCGTAAT CTGCTGCTTG
      AGTTTCCTAG AAGAACTCTA GGAAAAAAAG ACGCGCATTA GACGACGAAC
5451  CAAACAAAAA AACCACCGCT ACCAGCGGTG GTTTGTTTGC CGGATCAAGA
      GTTTGTTTTT TTGGTGGCGA TGGTCGCCAC CAAACAAACG GCCTAGTTCT
5501  GCTACCAACT CTTTTTCCGA AGGTAACTGG CTTCAGCAGA GCGCAGATAC
      CGATGGTTGA GAAAAAGGCT TCCATTGACC GAAGTCGTCT CGCGTCTATG
5551  CAAATACTGT CCTTCTAGTG TAGCCGTAGT TAGGCCACCA CTTCAAGAAC
      GTTTATGACA GGAAGATCAC ATCGGCATCA ATCCGGTGGT GAAGTTCTTG
5601  TCTGTAGCAC CGCCTACATA CCTCGCTCTG CTAATCCTGT TACCAGTGGC
      AGACATCGTG GCGGATGTAT GGAGCGAGAC GATTAGGACA ATGGTCACCG
5651  TGCTGCCAGT GGCGATAAGT CGTGTCTTAC CGGGTTGGAC TCAAGACGAT
      ACGACGGTCA CCGCTATTCA GCACAGAATG GCCCAACCTG AGTTCTGCTA
5701  AGTTACCGGA TAAGGCGCAG CGGTCGGGCT GAACGGGGGG TTCGTGCACA
      TCAATGGCCT ATTCCGCGTC GCCAGCCCGA CTTGCCCCCC AAGCACGTGT
5751  CAGCCCAGCT TGGAGCGAAC GACCTACACC GAACTGAGAT ACCTACAGCG
      GTCGGGTCGA ACCTCGCTTG CTGGATGTGG CTTGACTCTA TGGATGTCGC
5801  TGAGCATTGA GAAAGCGCCA CGCTTCCCGA AGGGAGAAAG GCGGACAGGT
      ACTCGTAACT CTTTCGCGGT GCGAAGGGCT TCCCTCTTTC CGCCTGTCCA
5851  ATCCGGTAAG CGGCAGGGTC GGAACAGGAG AGCGCACGAG GGAGCTTCCA
      TAGGCCATTC GCCGTCCCAG CCTTGTCCTC TCGCGTGCTC CCTCGAAGGT
5901  GGGGGAAACG CCTGGTATCT TTATAGTCCT GTCGGGTTTC GCCACCTCTG
      CCCCCTTTGC GGACCATAGA AATATCAGGA CAGCCCAAAG CGGTGGAGAC
5951  ACTTGAGCGT CGATTTTTGT GATGCTCGTC AGGGGGGCGG AGCCTATGGA
      TGAACTCGCA GCTAAAAACA CTACGAGCAG TCCCCCCGCC TCGGATACCT
6001  AAAACGCCAG CAACGCGGCC TTTTTACGGT TCCTGGCCTT TTGCTGGCCT
      TTTTGCGGTC GTTGCGCCGG AAAAATGCCA AGGACCGGAA AACGACCGGA
6051  TTTGCTCACA TGTTCTTTCC TGCGTTATCC CCTGATTCTG TGGATAACCG
      AAACGAGTGT ACAAGAAAGG ACGCAATAGG GGACTAAGAC ACCTATTGGC
6101  TATTACCGCC TTTGAGTGAG CTGATACCGC TCGCCGCAGC CGAACGACCG
      ATAATGGCGG AAACTCACTC GACTATGGCG AGCGGCGTCG GCTTGCTGGC
6151  AGCGCAGCGA GTCAGTGAGC GAGGAAGCGG AAG
      TCGCGTCGCT CAGTCACTCG CTCCTTCGCC TTC
```

FIGURE 3F

```
1201  AGCCACAAAT TATAATATAT AAAACACTAT ACAAAGTATC CAAATAAAGC CTAATAGGTA TGGAGGGTAA CCTGAATCTT TCCTAATAAT AATGAATAAT
      TCGGTGTTTA ATATTATATA TTTTGTGATA TGTTTCATAG GTTTATTTCG GATTATCCAT ACCTCCCATT GGACTTAGAA AGGATTATTA TTACTTATTA
                                                                                         ~~~~~~~~~~
                                                                                           BstEII

1301  CTACAATAAT GATTTGTTTG GACAAAGAGA ATTAAACGGT ATTGAGTGGG CTAAAATTCC TTGTTATTCA AAACCCTCAA TCACAGTTTC TCCGAGGGAA
      GATGTTATTA CTAAACAAAC CTGTTTCTCT TAATTGCCA  TAACTCACCC GATTTTAAGG AACAATAAGT TTTGGGAGTT AGTGTCAAAG AGGCTCCCTT

1401  AAAGAAACAG GGGAGGACAC TCAAGGCTGT CACAATAGGG ATTTCATATC GCTCTTTCCA ACAATCGCCAC ATCATCAAAA GTGTTATGAA ACTAAAAATG
      TTTCTTTGTC CCCTCCGTG  AGTCCGACAA GTGTTATCCC TAAAGTATAG CGAGAAAGGT TGTTACGGTG  TAGTAGTTTT CACAATACTT TGATTTTAC

1501  AAATAATACT TCTCAATGCA AACTTTCATT TTCATAGATT AATATACTAA TTAAATGATG CAACTAAAATA ACCAATAGAT GTTAGTAAAA TATGGTAAGA
      TTTATTATGA AGAGTTACGT TTGAAAGTAA AAGTATCTAA TTATATGATT AATTTACTAC GTTGATTTAT TGGTTATCTA CAATCATTTT ATACCATTCT

1601  TTAAACAAAC CACTATCAAT GGACATTTCA CATAGTTTCC AAGACTTTGA AAACCGGTTG ACATGATTTC ATCCACATCA AACTAATTTT ATCTCTGAAA
      AATTTGTTTG GTGATAGTTA CCTGTAAAGT GTATCAAAGG TTCTGAAACT TTTGCCCAAC TGTACTAAAG TAGGTGTAGT TTGATTAAAA TAGAGACTTT
                                   ~~~~~~~~~~~~
                                   short clone star 1701  CCCATTCATT TTAAATGATA TGGCATAACG TCCAAAATGC TACGTGACA  TACCATTAAA TGTGCATGAA ACTCCCATAA AACTTTTATT GATAATAGCC
      GGGTAAGTAA AATTTACTAT ACCGTATTGC AGGTTTTACG ACTGCACTGT ATGGTAATTT ACACGTACTT TGAGGGTATT TTGAAAATAA CTATTATCGG
                ~~~~~~~~~~~~
                tb1 binding sit 1801  TCACAGACAT CCGGTCCTAC ACCCGTGTGG ACCCATCAGC CAGACGCCCT GCAGCAAACG CGACGTTTGA CTTGCCATCT CGCTCCCTTG TGCCCGACCG
      AGTGTCTGTA GGCCAGGATG TGGGCACACC TGGGCAGTCG GTCTGCGGGA CGTCGTTTGC GCTGCAAACT GAACGGTAGA GCGAGGGAAC ACGGGCTGGC
                                                                            ~~~~
                                                                            PstI 1901  ACCCTGGAAG GCTGGACTGG AACTGGAACA AGCAAAATGG TCGTTTTGT  TCGACCTTGT TAGAGTGGTG ATCTCACCAC CCTTCCGGCC CACGCCAGGC TCGACCAATC
      TGGGACCTTC CGACCTGACC TTGACCTTGT TCGTTTTACC AGCAAAACAT TTTTTTGGTA ATCTCACCAC TAGAGTGGTG  GGAAGGCCGG GTGCGGTCCG AGCTGGTTAG 2001  CCTGCCCCGC GCGGGCCTGA CTCGAACGCC GAGCGCATCA CTCGAACGCC GAGCTTGCGG CCGGAGCGAT CCGGGTAGGA AGACCGGGCG TTATTGCTAG GGGCAGTACT AGGCTGCCAG
      GGACGGGCG  CGCGGGACTG GAGCTTGCGG CTCGCGTAGT GAGCTTGCGG GCCTCGCTA   GGCCCATCCT CCGGGTAGGA AGACCGGGCG TTATTGCTAG GGGCAGTACT AGGCTGCCAG 2101  TAGCTGCCTC CACGCCGCTC CAAAACCCCC GCGTCCAATC AAAACACGAC AGCGGGACGA GCGAAACCAC CGTGGTTTCG CCAAAACCGC TTCCTTCCCA
      ATCGACGGAG GTGCGGCGAG GTTTTGGGGG CGCAGGTTAG TTTTGTGCTG TCGCCCTGCT CGCTTTTGGTG GCACCAAAGC GGTTTGGCGA AAGGAAGGGT
                                      ~~~~~~~~~~~~~~~~~~~~~~~~~~
                                      p0092.chwaj31r & p0004.cb1hx
                                   ~~~~
                                   XhoI 2201  TCTAAAACCG CCCCCTCCCT TCCTCTTCTC CTAGCTCTCT TGCCTGCGCA CCATTCGAGT CGAGACTCGA GAGGCACCTG ATCTTTC
      AGATTTTGGC GGGGGAGGGA AGGAGAAGAG GATCGAGAGA ACGGACGCGT GGTGAGCTCA GCTCTGAGCT CTCCGTGGAC TAGAAAG
                                                                              ~~~~~~~~
                                                                              53489
```

FIGURE 5B short clone start p0092.chwaj31r & p0004.cb1hd54r

751 GGTCTCTGGT TCCAAGAATC TTTGTCTCTC TTTATGATAA TAACTTCTTT
    CCAGAGACCA AGGTTCTTAG AAACAGAGAG AAATACTATT ATTGAAGAAA short clone start p0092.chwaj31r & p0004.cb1hd54r 801 TGTCGTCCTT TTCTGTTTAC TTTGACTCAG GGGCAGTGCT TTGATTCTCA
    ACAGCAGGAA AAGACAAATG AAACTGAGTC CCCGTCACGA AACTAAGAGT short clone start p0092.chwaj31r & p0004.cb1hd54r 851 CGGTCGGTCC TTTTGACTGA GTGACTGGAC ATGTTTCTTC TGTAGCATTG
    GCCAGCCAGG AAAACTGACT CACTGACCTG TACAAAGAAG ACATCGTAAC short clone start p0092.chwaj31r & p0004.cb1hd54r 901 TACAACATGT ACTTTGTGCA AGCTACAAGG CCACATTTTT TGAAGCATAG
    ATGTTGTACA TGAAACACGT TCGATGTTCC GGTGTAAAAA ACTTCGTATC short clone start p0092.chwaj31r & p0004.cb1hd54r 951 ATTCTTTCCC CCAAACAATT TATACAAATA TGCAAGGCTA CACTTCTTGT
    TAAGAAAGGG GGTTTGTTAA ATATGTTTAT ACGTTCCGAT GTGAAGAACA short clone start p0092.chwaj31r & p0004.cb1hd54r HindIII
1001 ATTTCTATAA CATTGTACAT TCATGACAGA GGCTCAAAAG CTTGTAAATT
     TAAAGATATT GTAACATGTA AGTACTGTCT CCGAGTTTTC GAACATTTAA short clone start p0092.chwaj31r & p0004.cb1hd54r 1051 TTGTGCAGGT TTAATTCATG TAAAGTTCCC TTGTAGAGTC ATGACAACAT
     AACACGTCCA AATTAAGTAC ATTTCAAGGG AACATCTCAG TACTGTTGTA short clone start p0092.chwaj31r & p0004.cb1hd54r 1101 CGTACTATAA AATTATTCTA CAAAAACCAC ACATGACCCC CATGTTATTT
     GCATGATATT TTAATAAGAT GTTTTTGGTG TGTACTGGGG GTACAATAAA

FIGURE 5C short clone  start p0092.chwaj31r  &  p0004.cb1hd54r

1151 GGTGACAATA CAGAAACCAC ACATCTAGTG ATGATATAAC ACTGTACAGA
     CCACTGTTAT GTCTTTGGTG TGTAGATCAC TACTATATTG TGACATGTCT

--- short clone  start p0092.chwaj31r  &  p0004.cb1hd54r

1201 AGCCACAAAT TATAATATAT AAAACACTAT ACAAAGTATC CAAATAAAGC
     TCGGTGTTTA ATATTATATA TTTTGTGATA TGTTTCATAG GTTTATTTCG

--- short clone  start p0092.chwaj31r  &  p0004.cb1hd54r

BstEII
                 ~~~~~~~~
1251 CTAATAGGTA TGGAGGGTAA CCTGAATCTT TCCTAATAAT AATGAATAAT
     GATTATCCAT ACCTCCCATT GGACTTAGAA AGGATTATTA TTACTTATTA

--- short clone  start p0092.chwaj31r  &  p0004.cb1hd54r

1301 CTACAATAAT GATTTGTTTG GACAAAGAGA ATTAAACGGT ATTGAGTGGG
     GATGTTATTA CTAAACAAAC CTGTTTCTCT TAATTTGCCA TAACTCACCC

--- short clone  start p0092.chwaj31r  &  p0004.cb1hd54r

1351 CTAAAATTCC TTGTTATTCA AAACCCTCAA TCACAGTTTC TCCGAGGGAA
     GATTTTAAGG AACAATAAGT TTTGGGAGTT AGTGTCAAAG AGGCTCCCTT

--- short clone  start p0092.chwaj31r  &  p0004.cb1hd54r

1401 AAAGAAACAG GGGAGGACAC TCAGGCTGTT CACAATAGGG ATTTCATATC
     TTTCTTTGTC CCCTCCTGTG AGTCCGACAA GTGTTATCCC TAAAGTATAG

--- short clone  start p0092.chwaj31r  &  p0004.cb1hd54r

1451 GCTCTTTCCA ACAATGCCAC ATCATCAAAA GTGTTATGAA ACTAAAAATG
     CGAGAAAGGT TGTTACGGTG TAGTAGTTTT CACAATACTT TGATTTTTAC

--- short clone  start p0092.chwaj31r  &  p0004.cb1hd54r

1501 AAATAATACT TCTCAATGCA AACTTTCATT TTCATAGATT AAATATACTAA
     TTTATTATGA AGAGTTACGT TTGAAAGTAA AAGTATCTAA TTATATGATT

FIGURE 5D

```
         short clone start p0092.chwaj31r  &  p0004.cb1hd54r

1551  TTAAATGATG CAACTAAATA ACCAATAGAT GTTAGTAAAA TATGGTAAGA
      AATTTACTAC GTTGATTTAT TGGTTATCTA CAATCATTTT ATACCATTCT short clone start p0092.chwaj31r  &  p0004.cb1hd54r 1601  TTAAACAAAC CACTATCAAT GGACATTTCA CATAGTTTCC AAGACTTTGA
      AATTTGTTTG GTGATAGTTA CCTGTAAAGT GTATCAAAGG TTCTGAAACT short clone start p0092.chwaj31r  &  p0004.cb1hd54r 1651  AAACGGGTTG ACATGATTTC ATCCACATCA AACTAATTTT ATCTCTGAAA
      TTTGCCCAAC TGTACTAAAG TAGGTGTAGT TTGATTAAAA TAGAGACTTT short clone start
              short   clone start
                        =
         p0092.chwaj31r  &  p0004.cb1hd54r 1701  CCCATTCATT TTAAATGATA TGGCATAACG TCCAAAATGC TGACGTGACA
      GGGTAAGTAA AATTTACTAT ACCGTATTGC AGGTTTTACG ACTGCACTGT short clone start p0092.chwaj31r  &  p0004.cb1hd54r 1751  TACCATTAAA TGTGCATGAA ACTCCCATAA AACTTTTATT GATAATAGCC
      ATGGTAATTT ACACGTACTT TGAGGGTATT TTGAAAATAA CTATTATCGG p0092.chwaj31r  &  p0004.cb1hd54r short clone start        tbl binding site PstI
1801  TCACAGACAT CCGGTCCTAC ACCCGTGTGG ACCCATCAGC CAGACGCCCT
      AGTGTCTGTA GGCCAGGATG TGGGCACACC TGGGTAGTCG GTCTGCGGGA short clone start p0092.chwaj31r  &  p0004.cb1hd54r PstI 1851  GCAGCAAACG CGACGTTTGA CTTGCCATCT CGCTCCCTTG TGCCCGACCG
      CGTCGTTTGC GCTGCAAACT GAACGGTAGA GCGAGGGAAC ACGGGCTGGC short clone start p0092.chwaj31r  &  p0004.cb1hd54r 1901  ACCCTGGAAG GCTGGACTGG AACTGGAACA AGCAAAATGG AAAAAACCAT
      TGGGACCTTC CGACCTGACC TTGACCTTGT TCGTTTTACC TTTTTTGGTA
```

FIGURE 5E short clone    start p0092.chwaj31r   & p0004.cb1hd54r

1951  ATCTCACCAC TGAACCGCAC CCTTCCGGCC CACGCCAGGC TCGACCAATC
      TAGAGTGGTG ACTTGGCGTG GGAAGGCCGG GTGCGGTCCG AGCTGGTTAG short clone    start p0092.chwaj31r   & p0004.cb1hd54r 2001  CCTGCCCCGC GCGCCCTGAC GAGCGCATCA CTCGAACGCC GGCCTCGCTA
      GGACGGGGCG CGCGGGACTG CTCGCGTAGT GAGCTTGCGG CCGGAGCGAT short clone    start p0092.chwaj31r   & p0004.cb1hd54r 2051  GGCCCATCCT TCTGGCCCGC AATAACGATC CCCGTCATGA TCCGACGGTC
      CCGGGTAGGA AGACCGGGCG TTATTGCTAG GGGCAGTACT AGGCTGCCAG short clone    start p0092.chwaj31r   & p0004.cb1hd54r 2101  TAGCTGCCTC CACGCCGCTC CAAAACCCCC GCGTCCAATC AAAACACGAC
      ATCGACGGAG GTGCGGCGAG GTTTTGGGGG CGCAGGTTAG TTTTGTGCTG short clone    start p0092.chwaj31r   & p0004.cb1hd54r 2151  AGCGGGACGA GCGAAACCAC CGTGGTTTCG CCAAACCGCT TTCCTTCCCA
      TCGCCCTGCT CGCTTTGGTG GCACCAAAGC GGTTTGGCGA AAGGAAGGGT p0092.chwaj31r   & p0004.cb1hd54r short clone    start    p0092.chwaj31r   & p0004.cb1hd54r
                                                           =
2201  TCTAAAACCG CCCCCTCCCT TCCTCTTCTC CTAGCTCTCT TGCCTGCGCA
      AGATTTTGGC GGGGGAGGGA AGGAGAAGAG GATCGAGAGA ACGGACGCGT short clone    start p0092.chwaj31r   & p0004.cb1hd54r XhoI        XhoI
          ~~~~~       ~~~~~
          AvaI        AvaI
          ~~~~~       ~~~~~
2251  CCACTCGAGT CGAGACTCGA GAGGCACCTG ATCTTTC
      GGTGAGCTCA GCTCTGAGCT CTCCGTGGAC TAGAAAG
                              53489

FIGURE 5F

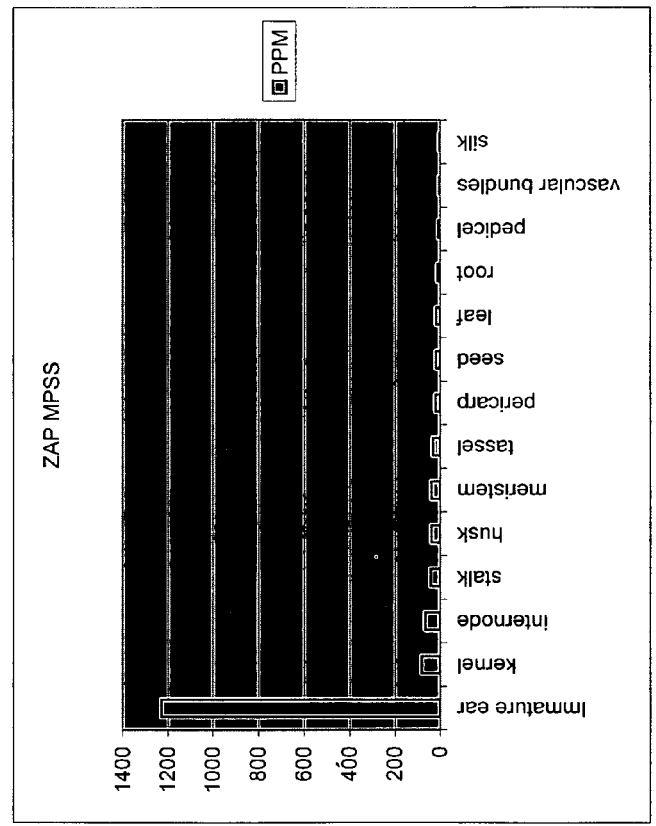
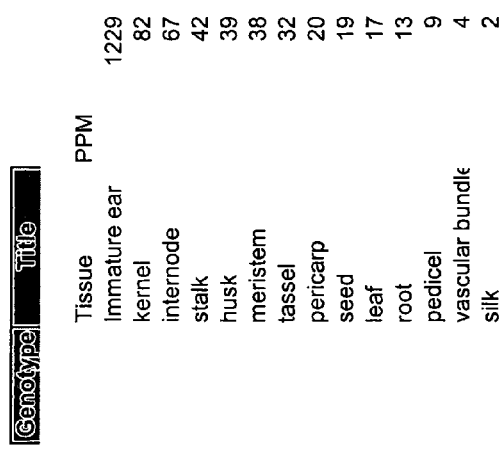
Figure 6

SEQUENCE LISTING

<160> NUMBER OF SEQ ID NOS: 7

<210> SEQ ID NO 1
<211> LENGTH: 2197
<212> TYPE: DNA
<213> ORGANISM: Zea mays

<400> SEQUENCE: 1

```
cctttttctt tttctccaca acatgaacct tactagaaca ctgccccact taaaagaatg      60
agggtagaac tcttgaatct tagggatttg aactccttgc agtacctcat aacaagggtg     120
ttacatgtcc ttcttctgct gttgctgctt gagcaggata tagagagatg accgacaccg     180
ggttgatctt gggacaacct tcttctcatc ttttcttcgt tgttttcttt tctattctca     240
ctacctttt ctttctcttt gttcttccca ctggaggatt ctatcaaaaa gtattaccat      300
catacagagg aggaacccga agactatgaa ccatgtacaa cagtcttcaa cccaagaatc     360
accaagcatt gtgatcttag gggcgaggga gtggaaaatg gagttgcttg tgatttggca     420
gagggaattt tatcaggagt gttttgcttt gagtggaatg gaactgagg gagttgttgg      480
ggggggggg tttataggcg agtgggagtg ctcgggtgcg gagtgtggtg atggaacagg      540
tgacatgagg tagcaggtcg atggaggggg gctgttgccg gcgatgatgg cggcggtggg     600
tgcgctgcaa aggagggcgt ggggcggtgg tagtgcgcat ggaggcgggc acgcgtgcgg     660
ggggcacaag tgagtggtgg ggtcgatgac cctgatgttt gtggtctctg gttccaagaa     720
tctttgtctc tctttatgat aataacttct tttgtcgtcc ttttctgttt actttgactc     780
aggggcagtg ctttgattct cacggtcggt ccttttgact gagtgactgg acatgtttct     840
tctgtagcat tgtacaacat gtactttgtg caagctacaa ggccacattt tttgaagcat     900
agattctttc ccccaaacaa tttatacaaa tatgcaaggc tacacttctt gtatttctat     960
aacattgtac attcatgaca gaggctcaaa agcttgtaaa ttttgtgcag gtttaattca    1020
tgtaaagttc ccttgtagag tcatgacaac atcgtactat aaaattattc tacaaaaacc    1080
acacatgacc cccatgttat ttggtgacaa tacagaaacc acacatctag tgatgatata    1140
acactgtaca gaagccacaa attataatat ataaaacact atacaaagta tccaaataaa    1200
gcctaatagg tatggagggt aacctgaatc tttcctaata ataatgaata atctacaata    1260
atgatttgtt tggacaaaga gaattaaacg gtattgagtg ggctaaaatt ccttgttatt    1320
caaaccctc aatcacagtt tctccgaggg aaaagaaac aggggaggac actcaggctg      1380
ttcacaatag ggatttcata tcgctctttc caacaatgcc acatcatcaa agtgttatg     1440
aaactaaaaa tgaaataata cttctcaatg caaacttttca ttttcataga ttaatatact    1500
aattaaatga tgcaactaaa taccaatag atgttagtaa aatatggtaa gattaaacaa     1560
accactatca atggacattt cacatagttt ccaagacttt gaaaacgggt tgacatgatt    1620
tcatccacat caaactaatt ttatctctga aacccattca ttttaaatga tatggcataa    1680
cgtccaaaat gctgacgtga cataccatta aatgtgcatg aaactcccat aaaactttta    1740
ttgataatag cctcacagac atccggtcct acaccgtgt ggacccatca gccagacgcc     1800
ctgcagcaaa cgcgacgttt gacttgccat ctcgctccct tgtgcccgac cgaccctgga    1860
aggctggact ggaactggaa caagcaaaat ggaaaaaacc atatctcacc actgaaccgc    1920
acccttccgg cccacgccag gctcgaccaa tccctgcccc gcgcgccctg acgagcgcat    1980
cactcgaacg ccggcctcgc taggcccatc cttctggccc gcaataacga tccccgtcat    2040
```

```
gatccgacgg tctagctgcc tccacgccgc tccaaaaccc ccgcgtccaa tcaaaacacg   2100
acagcgggac gagcgaaacc accgtggttt cgccaaaccg ctttccttcc catctaaaac   2160
cgccccctcc cttcctcttc tcctagctct cttgcct                            2197

<210> SEQ ID NO 2
<211> LENGTH: 6183
<212> TYPE: DNA
<213> ORGANISM: Artificial Sequence
<220> FEATURE:
<223> OTHER INFORMATION: synthetic

<400> SEQUENCE: 2
agcgcccaat acgcaaaccg cctctccccg cgcgttggcc gattcattaa tgcagctggc     60
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
ttgtgagcgg ataacaattt cacacaggaa acagctatga ccatgattac gccaagcttg    240
gtaccgagct cggatccact agtaacggcc gccagtgtgc tggaattcgc ccttactata    300
gggcacgcgt ggtcgacggc ccgggctggt ccttttttctt tttctccaca acatgaacct    360
tactagaaca ctgccccact taaaagaatg agggtagaac tcttgaatct tagggatttg    420
aactccttgc agtacctcat aacaagggtg ttacatgtcc ttcttctgct gttgctgctt    480
gagcaggata tagagagatg accgacaccg ggttgatctt gggacaacct tcttctcatc    540
ttttcttcgt tgttttcttt tctattctca ctacctttt ctttctcttt gttcttccca    600
ctggaggatt ctatcaaaaa gtattaccat catacagagg aggaacccga agactatgaa    660
ccatgtacaa cagtcttcaa cccaagaatc accaagcatt gtgatcttag gggcgaggga    720
gtggaaaatg gagttgcttg tgatttggca gagggaattt tatcaggagt gttttgcttt    780
gagtggaatg gaactgagg gagttgttgg ggggggggg tttataggcg agtgggagtg    840
ctcgggtgcg gagtgtggtg atggaacagg tgacatgagg tagcaggtcg atggagggg    900 gctgttgccg gcgatgatgg cggcggtggg tgcgctgcaa aggagggcgt ggggcggtgg    960
tagtgcgcat ggaggcgggc acgcgtgcgg ggggcacaag tgagtggtgg ggtcgatgac   1020
cctgatgttt gtggtctctg gttccaagaa tctttgtctc tctttatgat aataacttct   1080
tttgtcgtcc ttttctgttt actttgactc aggggcagtg ctttgattct cacggtcggt   1140
ccttttgact gagtgactgg acatgttct tctgtagcat tgtacaacat gtactttgtg    1200
caagctacaa ggccacattt tttgaagcat agattctttc ccccaaacaa tttatacaaa   1260
tatgcaaggc tacacttctt gtatttctat aacattgtac attcatgaca gaggctcaaa   1320
agcttgtaaa ttttgtgcag gtttaattca tgtaaagttc ccttgtagag tcatgacaac   1380
atcgtactat aaaattattc tacaaaaacc acacatgacc cccatgttat ttggtgacaa   1440
tacagaaacc acacatctag tgatgatata acactgtaca gaagccacaa attataatat   1500
ataaaacact atacaaagta tccaaataaa gcctaatagg tatggagggt aacctgaatc   1560
tttcctaata ataatgaata atctacaata atgatttgtt tggacaaaga gaattaaacg   1620
gtattgagtg ggctaaaatt ccttgttatt caaaaccctc aatcacagtt tctccgaggg   1680 aaaagaaac aggggaggac actcaggctg ttcacaatag ggatttcata tcgctctttc   1740
caacaatgcc acatcatcaa aagtgttatg aaactaaaaa tgaaataata cttctcaatg   1800
caaactttca ttttcataga ttaatatact aattaaatga tgcaactaaa taaccaatag   1860
```

-continued

```
atgttagtaa aatatggtaa gattaaacaa accactatca atggacattt cacatagttt    1920
ccaagacttt gaaaacgggt tgacatgatt tcatccacat caaactaatt ttatctctga    1980
aacccattca ttttaaatga tatggcataa cgtccaaaat gctgacgtga cataccatta    2040
aatgtgcatg aaactcccat aaaactttta ttgataatag cctcacagac atccggtcct    2100
acacccgtgt ggacccatca gccagacgcc ctgcagcaaa cgcgacgttt gacttgccat    2160
ctcgctccct tgtgcccgac cgaccctgga aggctggact ggaactggaa caagcaaaat    2220
ggaaaaaacc atatctcacc actgaaccgc acccttccgg cccacgccag gctcgaccaa    2280
tccctgcccc gcgcgccctg acgagcgcat cactcgaacg ccggcctcgc taggcccatc    2340
cttctggccc gcaataacga tccccgtcat gatccgacgg tctagctgcc tccacgccgc    2400
tccaaaaccc ccgcgtccaa tcaaaacacg acagcgggac gagcgaaacc accgtggttt    2460
cgccaaaccg cttccttcc catctaaaac cgcccctcc cttcctcttc tcctagctct    2520
cttgcctgcg caccactcga gtcgagactc gagaggcacc tgatctttca agggcgaatt    2580
ctgcagatat ccatcacact ggcggccgct cgagcatgca tctagagggc ccaattcgcc    2640
ctatagtgag tcgtattaca attcactggc cgtcgtttta caacgtcgtg actgggaaaa    2700
ccctggcgtt acccaactta atcgccttgc agcacatccc cctttcgcca gctggcgtaa    2760
tagcgaagag gcccgcaccg atcgcccttc ccaacagttg cgcagcctga atggcgaatg    2820
ggacgcgccc tgtagcggcg cattaagcgc ggcgggtgtg gtggttacgc gcagcgtgac    2880
cgctacactt gccagcgccc tagcgcccgc tcctttcgct ttcttccctt cctttctcgc    2940
cacgttcgcc ggctttcccc gtcaagctct aaatcggggg ctcccttag ggttccgatt    3000
tagagcttta cggcacctcg accgcaaaaa acttgatttg ggtgatggtt cacgtagtgg    3060
gccatcgccc tgatagacgg ttttcgccc tttgacgttg gagtccacgt tctttaatag    3120
tggactcttg ttccaaactg gaacaacact caacccctatc gcggtctatt cttttgattt    3180
ataagggatt ttgccgattt cggcctattg gttaaaaaat gagctgattt aacaaattca    3240
gggcgcaagg gctgctaaag gaaccggaac acgtagaaag ccagtccgca gaaacggtgc    3300
tgaccccgga tgaatgtcag ctactgggct atctggacaa gggaaaacgc aagcgcaaag    3360
agaaagcagg tagcttgcag tgggcttaca tggcgatagc tagactgggc ggttttatgg    3420
acagcaagcg aaccggaatt gccagctggg gcgccctctg gtaaggttgg aagccctgc    3480
aaagtaaact ggatggcttt cttgccgcca aggatctgat ggcgcagggg atcaagatct    3540
gatcaagaga caggatgagg atcgtttcgc atgattgaac aagatggatt gcacgcaggt    3600
tctccggccg cttgggtgga gaggctattc ggctatgact gggcacaaca gacaatcggc    3660
tgctctgatg ccgccgtgtt ccggctgtca gcgcaggggc gcccggttct ttttgtcaag    3720
accgacctgt ccggtgccct gaatgaactg caggacgagg cagcgcggct atcgtggctg    3780
gccacgacgg gcgttccttg cgcagctgtg ctcgacgttg tcactgaagc gggaagggac    3840
tggctgctat tgggcgaagt gccggggcag gatctcctgt catctcgcct tgctcctgcc    3900
gagaaagtat ccatcatggc tgatgcaatg cggcggctgc atacgcttga tccggctacc    3960
tgcccattcg accaccaagc gaaacatcgc atcgagcgag cacgtactcg gatggaagcc    4020
ggtcttgtcg atcaggatga tctggacgaa gagcatcagg gctcgcgcc agccgaactg    4080
ttcgccaggc tcaaggcgcg catgcccgac ggcgaggatc tcgtcgtgat ccatggcgat    4140
gcctgcttgc cgaatatcat ggtggaaaat ggccgctttt ctggattcaa cgactgtggc    4200
cggctgggtg tggcggaccg ctatcaggac atagcgttgg ataccgtga tattgctgaa    4260
```

```
gagcttggcg gcgaatgggc tgaccgcttc ctcgtgcttt acggtatcgc cgctcccgat    4320
tcgcagcgca tcgccttcta tcgccttctt gacgagttct tctgaattga aaaggaaga    4380 gtatgagtat tcaacatttc cgtgtcgccc ttattccctt ttttgcggca ttttgccttc    4440 ctgttttgc tcacccagaa acgctggtga agtaaaaga tgctgaagat cagttgggtg     4500
cacgagtggg ttacatcgaa ctggatctca acagcggtaa gatccttgag agttttcgcc    4560
ccgaagaacg ttttccaatg atgagcactt ttaaagttct gctatgtcat acactattat    4620
cccgtattga cgccgggcaa gagcaactcg gtcgccgggc gcggtattct cagaatgact    4680
tggttgagta ctcaccagtc acagaaaagc atcttacgga tggcatgaca gtaagagaat    4740
tatgcagtgc tgccataacc atgagtgata acactgcggc caacttactt ctgacaacga    4800
tcggaggacc gaaggagcta accgcttttt tgcacaacat gggggatcat gtaactcgcc    4860
ttgatcgttg ggaaccggag ctgaatgaag ccataccaaa cgacgagagt gacaccacga    4920
tgcctgtagc aatgccaaca acgttgcgca aactattaac tggcgaacta cttactctag    4980
cttcccggca acaattaata gactggatgg aggcggataa agttgcagga ccacttctgc    5040
gctcggccct tccggctggc tggtttattg ctgataaatc tggagccggt gagcgtgggt    5100
ctcgcggtat cattgcagca ctggggccag atggtaagcc ctcccgtatc gtagttatct    5160
acacgacggg gagtcaggca actatggatg aacgaaatag acagatcgct gagataggtg    5220
cctcactgat taagcattgg taactgtcag accaagttta ctcatatata ctttagattg    5280
atttaaaact tcatttttaa tttaaaagga tctaggtgaa gatcctttt gataatctca    5340 tgaccaaaat cccttaacgt gagttttcgt tccactgagc gtcagacccc gtagaaaaga    5400
tcaaaggatc ttcttgagat cctttttttc tgcgcgtaat ctgctgcttg caaacaaaaa    5460
aaccaccgct accagcggtg gtttgtttgc cggatcaaga gctaccaact ctttttccga    5520
aggtaactgg cttcagcaga gcgcagatac caaatactgt ccttctagtg tagccgtagt    5580
taggccacca cttcaagaac tctgtagcac cgcctacata cctcgctctg ctaatcctgt    5640
taccagtggc tgctgccagt ggcgataagt cgtgtcttac cgggttggac tcaagacgat    5700
agttaccgga taaggcgcag cggtcgggct gaacggggg ttcgtgcaca cagcccagct    5760
tggagcgaac gacctacacc gaactgagat acctacagcg tgagcattga aaagcgcca    5820 cgcttcccga agggagaaag gcggacaggt atccggtaag cggcagggtc ggaacaggag    5880
agcgcacgag ggagcttcca gggggaaacg cctggtatct ttatagtcct gtcgggtttc    5940
gccacctctg acttgagcgt cgatttttgt gatgctcgtc aggggggcgg agcctatgga    6000
aaaacgccag caacgcggcc ttttacggtt cctggccttt tgctggcct tttgctcaca     6060 tgttctttcc tgcgttatcc cctgattctg tggataaccg tattaccgcc tttgagtgag    6120
ctgataccgc tcgccgcagc cgaacgaccg agcgcagcga gtcagtgagc gaggaagcgg    6180
aag                                                                 6183
```

<210> SEQ ID NO 3
<211> LENGTH: 1331
<212> TYPE: DNA
<213> ORGANISM: Zea mays
<220> FEATURE:
<221> NAME/KEY: promoter
<222> LOCATION: (1)...(1331)

<400> SEQUENCE: 3

```
aagcttgtaa attttgtgca ggtttaattc atgtaaagtt cccttgtaga gtcatgacaa    60
```

```
catcgtacta taaaattatt ctacaaaaac cacacatgac ccccatgtta tttggtgaca      120
atacagaaac cacacatcta gtgatgatat aacactgtac agaagccaca aattataata      180
tataaaacac tatacaaagt atccaaataa agcctaatag gtatggaggg taacctgaat      240 cttcctaat aataatgaat aatctacaat aatgatttgt ttggacaaag agaattaaac       300
ggtattgagt gggctaaaat tccttgttat tcaaaaccct caatcacagt ttctccgagg      360 gaaaagaaa caggggagga cactcaggct gttcacaata gggatttcat atcgctcttt      420
ccaacaatgc cacatcatca aaagtgttat gaaactaaaa atgaaataat acttctcaat      480
gcaaactttc atttcatag attaatatac taattaaatg atgcaactaa ataaccaata      540
gatgttagta aaatatggta agattaaaca aaccactatc aatggacatt tcacatagtt      600
tccaagactt tgaaaacggg ttgacatgat ttcatccaca tcaaactaat tttatctctg      660
aaacccattc attttaaatg atatggcata acgtccaaaa tgctgacgtg acataccatt      720
aaatgtgcat gaaactccca taaaactttt attgataata gcctcacaga catccggtcc      780
tacacccgtg tggacccatc agccagacgc cctgcagcaa acgcgacgtt tgacttgcca      840
tctcgctccc ttgtgcccga ccgaccctgg aaggctggac tggaactgga acaagcaaaa      900
tggaaaaaac catatctcac cactgaaccg caccttccg gcccacgcca ggctcgacca      960
atccctgccc cgcgcgccct gacgagcgca tcactcgaac gccggcctcg ctaggcccat    1020
ccttctggcc cgcaataacg atcccgtca tgatccgacg gtctagctgc ctccacgccg     1080
ctccaaaacc cccgcgtcca atcaaaacac gacagcggga cgagcgaaac caccgtggtt    1140
tcgccaaacc gctttccttc ccatctaaaa ccgcccctc ccttcctctt ctcctagctc     1200
tcttgcctgc gcaccactcg agtcgagact cgagaggcac ctgatctttc cttcccgtct    1260
tcctcccaca cgtccccatc accattgctg cgacgagagt gagcgggaga gggtaggtgg    1320
cgaggcggcg g                                                         1331
```

<210> SEQ ID NO 4
<211> LENGTH: 1547
<212> TYPE: DNA
<213> ORGANISM: Zea mays
<220> FEATURE:
<221> NAME/KEY: promoter
<222> LOCATION: (1)...(1547)

<400> SEQUENCE: 4

```
ttgactcagg ggcagtgctt tgattctcac ggtcggtcct tttgactgag tgactggaca      60
tgtttcttct gtagcattgt acaacatgta ctttgtgcaa gctacaaggt cacattttt     120 gaagcataga ttctttcccc caaacaattt atacaaatat gcaaggctac acttcttgta    180
tttctataac attgtacatt catgacagag gctcaaaagc ttgtaaattt tgtgcaggtt    240
taattcatgt aaagttccct tgtagagtca tgacaacatc gtactataaa attattctac    300
aaaaaccaca catgaccccc atgttatttg gtgacaatac agaaaccaca catctagtga    360
tgatataaca ctgtacagaa gccacaaatt ataatatata aaacactata caaagtatcc    420
aaataaagcc taataggtat ggagggtaac ctgaatcttt cctaataata atgaataatc    480
tacaataatg atttgtttgg acaaagagaa ttaaacggta ttgagtgggc taaaattcct    540
tgttattcaa aaccctcaat cacagtttct ccgagggaaa agaaacagg ggaggacact     600 caggctgttc acaatagggga tttcatatcg ctctttccaa caatgccaca tcatcaaaag   660
tgttatgaaa ctaaaaatga aataatactt ctcaatgcaa actttcattt tcatagatta    720
```

```
atatactaat taaatgatgc aactaaataa ccaatagatg ttagtaaaat atggtaagat      780
taaacaaacc actatcaatg gacatttcac atagtttcca agactttgaa aacgggttga      840
catgatttca tccacatcaa actaatttta tctctgaaac ccattcattt taaatgatat      900
ggcataacgt ccaaaatgct gacgtgacat accattaaat gtgcatgaaa ctcccataaa      960
acttttattg ataatagcct cacagacatc cggtcctaca cccgtgtgga cccatcagcc     1020
agacgccctg cagcaaacgc gacgtttgac ttgccatctc gctcccttgt gcccgaccga     1080
ccctggaagg ctggactgga actgaacaa gcaaaatgga aaaaaccata tctcaccact      1140
gaaccgcacc cttccggccc acgccaggct cgaccaatcc ctgccccgcg cgccctgacg     1200
agcgcatcac tcgaacgccg gcctcgctag gcccatcctt ctggcccgca ataacgatcc     1260
ccgtcatgat ccgacggtct agctgcctcc acgccgctcc aaaaccccg cgtccaatca      1320 aaacacgaca gcgggacgag cgaaaccacc gtggtttcgc caaaccgctt ccttccccat     1380
ctaaaaccgc ccctcccctt cctcttctcc tagctctctt gcctgcgcac cactcgagtc     1440
gagactcgag aggcacctga tctttccttc ccgtcttcct cccacacgtc cccatcacca     1500
ttgctgcgac gagagtgagc gggagagggt aggtggcgag gcggcgg                   1547

<210> SEQ ID NO 5
<211> LENGTH: 1552
<212> TYPE: DNA
<213> ORGANISM: Zea mays
<220> FEATURE:
<221> NAME/KEY: promoter
<222> LOCATION: (1)...(1552)

<400> SEQUENCE: 5
gcccttgact caggggcagt gctttgattc tcacggtcgg tccttttgac tgagtgactg       60
gacatgtttc ttctgtagca ttgtacaaca tgtactttgt gcaagctaca aggtcacatt      120
ttttgaagca tagattcttt cccccaaaca atttatacaa atatgcaagg ctacacttct      180
tgtatttcta taacattgta cattcatgac agaggctcaa aagcttgtaa attttgtgca      240
ggtttaattc atgtaaagtt cccttgtaga gtcatgacaa catcgtacta taaaattatt      300
ctacaaaaac cacacatgac ccccatgtta tttggtgaca atacagaaac cacacatcta      360
gtgatgatat aacactgtac agaagccaca aattataata tataaaacac tatacaaagt      420
atccaaataa agcctaatag gtatggaggg taacctgaat ctttcctaat aataatgaat      480
aatctacaat aatgatttgt ttggacaaag agaattaaac ggtattgagt gggctaaaat      540
tccttgttat tcaaaaccct caatcacagt ttctccgagg gaaaagaaa caggggagga      600 cactcaggct gttcacaata gggatttcat atcgctcttt ccaacaatgc cacatcatca      660
aaagtgttat gaaactaaaa atgaaataat acttctcaat gcaaactttc attttcatag      720
attaatatac taattaaatg atgcaactaa ataaccaata gatgttagta aaatatggta      780
agattaaaca aaccactatc aatggacatt tcacatagtt tccaagactt tgaaaacggg      840
ttgacatgat tcatccaca tcaaactaat tttatctctg aaacccattc attttaaatg      900
atatggcata acgtccaaaa tgctgacgtg acataccatt aaatgtgcat gaaactccca      960
taaaactttt attgataata gcctcacaga catccggtcc tacacccgtg tggacccatc     1020
agccagacgc cctgcagcaa acgcgacgtt tgacttgcca tctcgctccc ttgtgcccga     1080
ccgaccctgg aaggctggac tggaactgga acaagcaaaa tggaaaaaac catatctcac     1140
cactgaaccg caccccttccg gcccacgcca ggctcgacca atccctgccc cgcgcgccct     1200
```

```
                                              -continued gacgagcgca tcactcgaac gccggcctcg ctaggcccat ccttctggcc cgcaataacg    1260
atccccgtca tgatccgacg gtctagctgc ctccacgccg ctccaaaacc cccgcgtcca    1320
atcaaaacac gacagcggga cgagcgaaac caccgtggtt tcgccaaacc gctttccttc    1380
ccatctaaaa ccgcccctc ccttcctctt ctcctagctc tcttgcctgc gcaccactcg    1440
agtcgagact cgagaggcac ctgatctttc cttcccgtct tcctcccaca cgtccccatc   1500
accattgctg cgacgagagt gagcgggaga gggtaggtgg cgaggcggcg gc           1552

<210> SEQ ID NO 6
<211> LENGTH: 30
<212> TYPE: DNA
<213> ORGANISM: Artificial Sequence
<220> FEATURE:
<223> OTHER INFORMATION: primer sequence

<400> SEQUENCE: 6
cccgctcact ctcgtcgcag caatggtgat                                     30

<210> SEQ ID NO 7
<211> LENGTH: 30
<212> TYPE: DNA
<213> ORGANISM: Artificial Sequence
<220> FEATURE:
<223> OTHER INFORMATION: primer sequence

<400> SEQUENCE: 7
gaaagatcag gtgcctctcg agtctcgact                                     30
```

EARLY-INFLORESCENCE-PREFERRED REGULATORY ELEMENTS AND USES THEREOF

CROSS-REFERENCE TO RELATED APPLICATIONS

This application is a continuation-in-part of U.S. Ser. No. 10/387,937, filed Mar. 13, 2003, now abandoned which claims priority to U.S. provisional application 60/364,065, filed Mar. 13, 2002, both of which are hereby incorporated by reference.

FIELD OF THE INVENTION

The present invention relates to the field of plant molecular biology, more particularly to regulation of gene expression in plants.

BACKGROUND OF THE INVENTION

Expression of isolated DNA sequences in a plant host is dependent upon the presence of operably-linked regulatory elements that are functional within the plant host. Choice of the regulatory sequences will determine when and where within the organism the isolated DNA sequence is expressed. Where continuous expression is desired throughout the cells of a plant, a constitutive promoter is utilized. In contrast, where gene expression in response to a stimulus is desired, an inducible promoter is the regulatory element of choice. Where expression in specific tissues or organs is desired, tissue-preferred promoters and/or terminators are used. That is, these regulatory elements can drive expression preferentially in specific tissues or organs. Additional regulatory sequences upstream and/or downstream from the core sequences can be included in expression cassettes of transformation vectors to bring about varying levels of expression of isolated nucleotide sequences in a transgenic plant. See, for example, U.S. Pat. No. 5,850,018.

Plants have two basic growth modes during their life cycles: vegetative growth and reproductive growth. The above-ground vegetative growth of the plant develops from the apical meristem. This vegetative meristem gives rise to all of the leaves that are found on the plant. The plant will maintain its vegetative growth pattern until the apical meristem undergoes a change. This change alters the identity of the meristem from a vegetative to an inflorescence meristem. The inflorescence meristem produce small leaves before it next produces floral meristems. It is the floral meristem from which the flower develops.

The floral meristem undergoes a series of developmental changes that eventually give rise to the four basic structures of the flower: sepals, petals, stamens and carpels. Each of these structures is derived sequentially from a whorl that develops from the floral meristem. The first whorl develops into the sepals of the plant. The second whorl develops into petals. The third and fourth whorls define the stamen (male reproductive organs) and carpel (female reproductive organs), respectively.

From a genetic perspective, two changes that control vegetative and floral growth are programmed into the plant. The first genetic change involves the switch from the vegetative to the floral state. If this genetic change is not functioning properly, then flowering will not occur. The second genetic event follows the commitment of the plant to form flowers. The observation that the organs of the plant develop in a sequential manner suggests that a genetic mechanism exists in which a series of genes are sequentially turned on and off. This switching is necessary for each whorl to obtain its final unique identity.

A series of *Arabidopsis* mutants have been identified in which normal flowers are replaced with structures that resemble inflorescence meristems and the shoots that normally develop from them. One such mutant is LEAFY. This mutant does not contain any normal flowers. Instead, the early flower structures that develop appear as inflorescence shoots, whereas the later flowers partially resemble normal flowers. These later-developing flowers contain sepal and carpel-like structures; however, they lack petals and stamens. This suggests that LEAFY has two functions: committing the plant to floral meristem development, and defining petals and stamens.

Another *Arabidopsis* gene affecting flower intiation and development is APETALA1, also known as AP1. The AP1 gene product has been classified as a MADS protein and acts as a transcription factor. Specific motifs within MADS proteins regulate binding to promoters of other genes involved in floral development. Interactions among the MADS proteins are also possible. Conserved regions include the MADS domain, the K-box, the I-region, and the C-region. Within the general class of MADS proteins are several families. AP1 falls within the SQUA family, members of which generally are involved in both floral meristem identity and in floral organ development. This is reflected in spatial expression differences; e.g., AP1 mRNA is observed throughout the floral meristem during early flower development, but only in the outer two whorls as sepal and petal development is initiated. AP1 acts within a complex network of regulatory genes; it appears to be positively regulated by LFY, and its expression is also dependent on flowering-related genes such as FT and FD. AP1 expression is negatively regulated by PISTILLATA (PI) and an interacting protein, APETALA3 (AP3). (See, Sundström, et al., *Plant Journal* 46:593-600 (2006); Jang, et al., *Plant Cell Physiol.* 43(1)230-238 (2002); Reichmann and Meyerowitz, *Biol. Chem.* 378:1079-1101 (1997); Mandel, et al., *Nature* 360: 273-277 (1992); Coen and Meyerowitz, *Nature* 353:31-37 (1991)) Flowers of APETALA1 (AP1) mutants are not altered as dramatically as LEAFY mutants. These mutants express a partial inflorescence meristem phenotype where secondary floral meristems appear in the axis region of the sepal. But when the APETALA1 and LEAFY mutants are combined, the flowers appear as an inflorescence shoot. The snapdragon analog to the APETALA1 gene, SQUAMOSA, is much more severe, and the flowers appear as inflorescence shoots. APETALA1 also affects the normal development of sepals and petals.

Cloning of the *Arabidopsis* genes involved in the commitment to flowering and the genes controlling flower organ development has been achieved either by heterologous probing with snapdragon genes or by transposon tagging.

AP1 genes have also been identified in maize. See, for example, Münster et al., *Maydica* 47:287-301 (2002) and GenBank accession ZMA430695.

Maize is a monocotyledonous plant species and belongs to the grass family. It is unusual for a flowering plant as it has unisexual inflorescences The male inflorescence (tassel) develops in a terminal position, whereas the female inflorescences (ears) grow in the axil of vegetative leaves. The inflorescences, as typical for grasses, are composed of spikelets. In the case of maize each spikelet contains two florets (the grass flower) enclosed by a pair of bracts (inner and outer glume).

The grass flower is sufficiently different from a typical angiosperm flower. The lafter is composed of concentric whorls of sepals and petals enclosing whorls of stamens and pistils. The homologies of the angiosperm flower-tissues to those of the grass floret have long been debated.

According to the invention, developmentally-specific regulatory sequences are disclosed which enable the transcription of genes during the critical time of inflorescence development, preferably in early flowering tissues such as meristems, to manipulate traits such as flowering time, flower initiation, and meristem development in plants.

Isolation and characterization of promoters and terminators active in early stages of flower development can serve as regulatory elements for expression of isolated nucleotide sequences of interest in a flowering-preferred manner and are useful for manipulations targeting improved flowering traits in plants.

SUMMARY OF THE INVENTION

The invention provides regulatory elements isolated from maize which are capable of driving expression in meristem and developing inflorescence tissues. The promoter is known as ZM-MADS PRO1, or ZAP (Zea mays APETALA), or AP1-like. The invention also comprises expression constructs comprising the regulatory elements of the invention operably linked to DNA sequences, vectors incorporating said expression constructs, plant cells transformed with these constructs and resultant plants regenerated from the same. The regulatory elements of the invention provide for expression of operably-linked sequences in tissues involved in flowering.

BRIEF DESCRIPTION OF THE DRAWINGS

FIG. 3 is the sequence SEQ ID NO: 2 of the PHP plasmid depicted in FIG. 2.

FIG. 6 shows tissue-preferred expression of the AP1-like gene as determined by MPSS™ analysis.

DETAILED DESCRIPTION OF THE INVENTION

Figure 1:
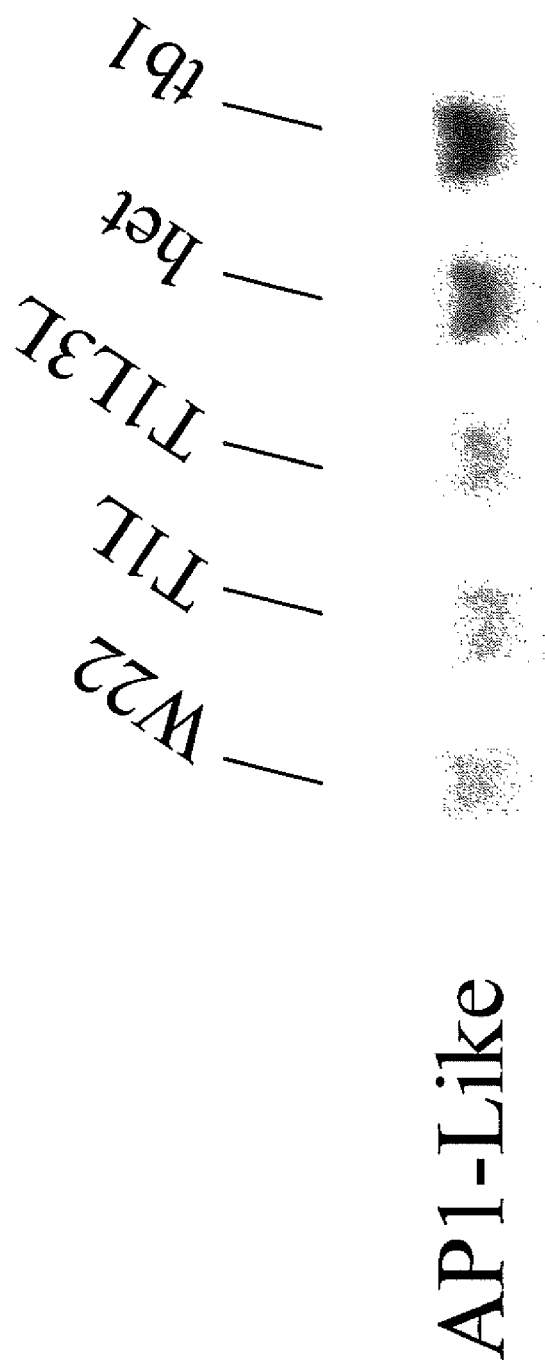
FIG. 1 is a Northern analysis of the maize AP1 gene expression in wild-type plant (W22), W22 plant introgressed with the teosinte 1L chromosome (T1L), W22 plant introgressed with the teosinte 1L and 3L chromosomes (T1L3L), T1/t1-mum3 heterozygote (het) and t1-mum3 homozygote (t1). All are in W22 background.

The AP1 gene regulates specific stages of flowering development in a range of species. In accordance with the invention, nucleotide sequences are provided that allow initiation of transcription in tissues involved in early flowering development such as meristem tissue, in an AP1-like expression pattern. The sequences of the invention comprise transcriptional initiation regions associated temporally with flower development and spatially with flower development tissues. Thus, the compositions of the present invention comprise novel nucleotide sequences for plant regulatory elements as described in more detail below.

A method for expressing an isolated nucleotide sequence in a plant using the transcriptional initiation sequences disclosed herein is provided. The method comprises transforming a plant cell with a transformation vector that comprises an isolated nucleotide sequence operably linked to one or more of the plant regulatory sequences of the present invention and regenerating a stably transformed plant from the transformed plant cell. In this manner, the regulatory sequences are useful for controlling the expression of endogenous as well as exogenous products in a flower-development-preferred manner.

Under the transcriptional initiation regulation of the flowering-development-specific region will be a sequence of interest, which will provide for modification of the phenotype of the developing flower. Such modification includes modulating the production of an endogenous product as to amount, relative distribution, or the like, or production of an exogenous expression product to provide for a novel function or product in the flower, manipulating the size of the flower, manipulating the time of flowering, length of flowering and the like.

By "flowering development" is intended favored expression in the newly developing inflorescence tissues, including but not limited to, meristem tissue.

By "regulatory element" is intended sequences responsible for spatially- and/or temporally-preferred expression of the associated coding sequence, including promoters, terminators, enhancers, introns, and the like.

By "terminator" is intended sequences that are needed for termination of transcription. A terminator is a regulatory region of DNA that causes RNA polymerase to disassociate from DNA, resulting in termination of transcription.

By "promoter" is intended a regulatory region of DNA, usually comprising a TATA box and capable of directing RNA polymerase II to initiate RNA synthesis at the appropriate transcription initiation site for a particular coding sequence. A promoter can additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements in the 5' untranslated region upstream from the particular promoter region identified herein. Thus the promoter region disclosed herein is generally further defined by comprising upstream regulatory elements such as those responsible for spatially- and temporally-preferred expression of the coding sequence, enhancers, and the like. In the same manner, the promoter elements which enable expression in the desired tissue, such as certain flower tissues, can be identified, isolated, and used with other core promoters to confirm early flowering-development-preferred expression.

The isolated promoter sequences of the present invention can be modified to provide for a range of expression levels of the isolated nucleotide sequence. Less than the entire promoter region can be utilized while retaining the ability to drive flowering development-preferred expression. However, it is recognized that expression levels of mRNA can be decreased with deletions of portions of the promoter sequence. Thus, the promoter can be modified to be a weak or strong promoter. Generally, by "weak promoter" is intended a promoter that drives expression of a coding sequence at a low level, i.e. about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts. Generally, at least about 20 nucleotides of an isolated promoter sequence will be used to drive expression of a nucleotide sequence.

It is recognized that to increase transcription levels, enhancers can be utilized in combination with the promoter regions of the invention. Enhancers are nucleotide sequences that act to increase the expression of a promoter region.

Enhancers are known in the art and include the SV40 enhancer region, the 35S enhancer element, and the like.

The promoters of the present invention can be isolated from the 5' untranslated region flanking its respective transcription initiation site. Likewise, the terminator can be isolated from the 3' untranslated region flanking its respective stop codon. The term "isolated" refers to material, such as a nucleic acid or protein, which is substantially or essentially free from components which normally accompany or interact with the material as found in its naturally-occurring environment; or, if the material is in its natural environment, the material has been altered by deliberate human intervention and/or placed at a locus in a cell other than the locus native to the material. Methods for isolation of promoter regions are well known in the art. A sequence for the promoter region is set forth in SEQ ID NO: 1. The A 1-like promoter set forth in SEQ ID NO: 1 is 2197 nucleotides in length. Additional functional AP1-like promoter sequences are provided in SEQ ID NOs: 3, 4, and 5.

The promoter regions of the invention may be isolated from any plant, including but not limited to corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatas*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus carica*), guava (*Psidium guajava*), mango (*Mangifera indica*), olive (*Olea europaea*), oats, barley, vegetables, ornamentals, and conifers. Preferably, plants include corn, soybean, sunflower, safflower, canola, wheat, barley, rye, alfalfa, and sorghum.

Promoter sequences from other plants may be isolated according to well-known techniques based on their sequence identity to the promoter sequences set forth herein. Alternatively, promoter sequences may be identified and isolated based on proximity to coding sequences orthologous to the endogenous coding sequence associated with the disclosed promoter sequences. In these techniques, all or part of the known sequence is used as a probe which selectively hybridizes to other sequences present in a population of cloned genomic DNA fragments (i.e., genomic libraries) from a chosen organism. Methods are readily available in the art for the hybridization of nucleic acid sequences. For example, see Sambrook & Russell, *Molecular Cloning: A Laboratory Manual*, 3$^{rd}$ ed., Cold Spring Harbor Laboratory Press, Cold Spring Harbor, N.Y. (2001).

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see e.g., Innis, et al., (1990) *PCR Protocols, A Guide to Methods and Applications*, eds., Academic Press).

The terms "stringent conditions" or "stringent hybridization conditions" includes reference to conditions under which a probe will hybridize to its target sequence to a detectably greater degree than to other sequences (e.g., at least 2-fold over background). Stringent conditions are target-sequence dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing).

An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995). See also, Sambrook, et al., (1989) *Molecular Cloning: A Laboratory Manual* (2nd ed. Cold Spring Harbor Laboratory, Cold Spring Harbor, N.Y.).

In general, sequences that correspond to the promoter sequence of the present invention and hybridize to the promoter sequence disclosed herein, or to its complement, will be at least 50% identical, 55% identical, 60% identical, 65% identical, 70% identical, 75% identical, 80% identical, 85% identical, 90% identical, 95% identical and even 98% or more identical to the disclosed sequence.

Specificity is typically the function of post-hybridization washes, the critical factors being the ionic strength and temperature of the final wash solution. Generally, stringent wash temperature conditions are selected to be about 5° C. to about 2° C. lower than the melting point ($T_m$) for the specific sequence at a defined ionic strength and pH. The melting point, or denaturation, of DNA occurs over a narrow temperature range and represents the disruption of the double helix into its complementary single strands. The process is described by the temperature of the midpoint of transition, $T_m$, which is also called the melting temperature. Formulas are available in the art for the determination of melting temperatures.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2× SSC (20× SSC=3.0 M NaCl/0.3 M trisodium citrate) at 50 to 55° C. Exemplary moderate stringency conditions include hybridization in 50 to 55% formamide, 1.0 M NaCl, 1% SDS at 37° C., and a wash in 0.5× to 1× SSC at 55 to 60° C. Exemplary high stringency conditions include hybridization in 50% formamide, 1 M NaCl, 1% SDS at 37° C., and a wash in 0.1× SSC at 60 to 65° C. Optionally, wash buffers may comprise about 0.1% to about 1% SDS. Duration of hybridization is generally less than about 25 hours, usually about 5 to about 12 hours. The duration of the wash time will be at least a length of time sufficient to reach equilibrium.

The following terms are used to describe the sequence relationships between two or more nucleic acids or polynucleotides: (a) "reference sequence", (b) "comparison window", (c) "percentage of sequence identity", and (d) "substantial identity".

(a) As used herein, "reference sequence" is a defined sequence used as a basis for sequence comparison. A reference sequence may be a subset or the entirety of a specified sequence; for example, a segment of a full-length promoter sequence, or the complete promoter sequence.

(b) As used herein, "comparison window" makes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length and optionally can be 30, 40, 50, 100 or more contiguous nucleotides in length. Those of skill in the art understand that to avoid a high similarity to a reference sequence due to inclusion of gaps in the polynucleotide sequence, a gap penalty is typically introduced and is subtracted from the number of matches.

(c) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

(d) The term "substantial identity" of polynucleotide sequences means that a polynucleotide comprises a sequence that has at least 70% sequence identity, preferably at least 80%, more preferably at least 90% and most preferably at least 95%, compared to a reference sequence, using one of the alignment programs described using standard parameters.

Methods of aligning sequences for comparison are well known in the art. Gene comparisons can be determined by conducting BLAST (Basic Local Alignment Search Tool; Altschul, S. F., et al., (1993) *J. Mol. Biol.* 215:403-410; see also www.ncbi.nlm.nih.gov/BLAST/) searches under default parameters for identity to sequences contained in the BLAST "GENEMBL" database. A sequence can be analyzed for identity to all publicly available DNA sequences contained in the GenBank database using the BLASTN algorithm under the default parameters. Identity to the sequence of the present invention would mean a polynucleotide sequence having at least 65%, 70%, 75%, 80%, 85%, 90%, 95% or higher sequence identity, wherein the percent sequence identity is based on the entire promoter region.

GAP uses the algorithm of Needleman and Wunsch (*J. Mol. Biol.* 48:443-453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. If a gap extension penalty greater than zero is chosen, GAP must, in addition, make a profit for each gap inserted of the length of the gap times the gap extension penalty. Default gap creation penalty values and gap extension penalty values in Version 10 of Accelrys GCG® (formerly GCG Wisconsin Package®) for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) *Proc. Natl. Acad. Sci. USA* 89:10915).

Sequence fragments with high percent identity to the sequences of the present invention also refer to those fragments of a particular regulatory element nucleotide sequence disclosed herein that operate to promote the early-flower-preferred expression of an operably-linked isolated nucleotide sequence. These fragments will comprise at least about 20, 50, 75 or 100 contiguous nucleotides of the particular promoter nucleotide sequences disclosed herein. The nucleotides of such fragments will usually comprise the TATA recognition sequence of the particular promoter sequence. Such fragments can be obtained by use of any of multiple techniques known to those of skill in the art, including restriction enzyme cleavage of the naturally-occurring regulatory element nucleotide sequences disclosed herein; synthesis of a nucleotide sequence based on the naturally occurring DNA sequence; or use of PCR technology. See particularly, Mullis, et al., (1987) *Methods Enzymol.* 155:335-350, and Erlich, ed. (1989) *PCR Technology* (Stockton Press, New York). Again, variants of these fragments, such as those resulting from site-directed mutagenesis, are encompassed by the compositions of the present invention.

Nucleotide sequences comprising at least about 20 contiguous sequences of the sequence set forth in SEQ ID NOS: 1, 3, 4, or 5 are encompassed. These sequences can be isolated by hybridization, PCR, and the like. Such sequences encompass fragments capable of driving early-flower-preferred expression, fragments useful as probes to identify similar sequences, and elements responsible for temporal or tissue specificity.

Biologically active variants of the regulatory sequences are also encompassed by the compositions of the present invention. A regulatory "variant" is a modified form of a regulatory sequence wherein one or more bases have been modified, removed or added. For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digests of a clone with this enzyme produces unidirectional nested deletions.

One example of a regulatory sequence variant is a promoter formed by one or more deletions from a larger promoter. The 5' portion of a promoter up to the TATA box near the transcription start site can be deleted without abolishing promoter activity, as described by Zhu, et al., *The Plant Cell* 7:1681-89 (1995). Such variants should retain promoter activity, particularly the ability to drive expression in inflorescence meristems, developing floral tissues, or other such tissues. Biologically active variants include, for example, the native regulatory sequences of the invention having one or more nucleotide substitutions, deletions or insertions. Activity can be measured by Northern blot analysis, reporter activity measurements when using transcriptional fusions, and the like. See, for example, Sambrook, et al., *Molecular Cloning: A Laboratory Manual* (Cold Spring Harbor Laboratory, Cold Spring Harbor, N.Y., $2^{nd}$ ed. 1989 or $3^{rd}$ ed. 2001), herein incorporated by reference.

The nucleotide sequences for the inflorescence-meristem-preferred regulatory elements disclosed in the present invention, as well as variants and fragments thereof, are useful in the genetic manipulation of any plant when operably linked with an isolated nucleotide sequence whose expression is to be controlled to achieve a desired phenotypic response. By "operably linked" is intended that the transcription or translation of the isolated nucleotide sequence is under the influence of the regulatory sequence. In this manner, the nucleotide sequences for the regulatory elements of the invention may be provided in expression cassettes along with isolated nucleotide sequences for expression in the plant of interest, more particularly in the developing flower of the plant. Such an expression cassette is provided with a plurality of restriction sites for insertion of the nucleotide sequence to be under the transcriptional control of the regulatory elements. Subsequently, a plant cell having the introduced sequence of the invention is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to modulate expression of polynucleotide sequences operably linked to the regulatory element of the invention.

It is also recognized that a plant or plant part may be modulated by expression of a polynucleotide that is not capable of directing, in a transformed plant, the expression of a protein or an RNA. For example, the polynucleotides of the invention can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774-8778; herein incorporated by reference.

The genes of interest expressed under control of the regulatory elements of the invention can be used for varying the phenotype of flowering development; in maize this may be reflected in ear development. This can be achieved by increasing expression of endogenous or exogenous products in the targeted tissue. Alternatively, the results can be achieved by providing for a reduction of expression of one or more endogenous products, particularly enzymes or cofactors, in the developing flower. These modifications result in a change in phenotype of the transformed plant. It is recognized that the regulatory elements may be used with their native coding sequences to increase or decrease expression resulting in a change in phenotype in the transformed plant.

General categories of genes of interest for the purposes of the present invention include for example, those genes involved in information, such as Zinc fingers; those involved in communication, such as kinases; and those involved in housekeeping, such as heat shock proteins. More specific categories of transgenes include genes encoding important traits for agronomics, insect resistance, disease resistance, herbicide resistance, and grain characteristics. Still other categories of transgenes include genes for inducing expression of exogenous products such as enzymes, cofactors, and hormones from plants and other eukaryotes as well as prokaryotic organisms. It is recognized that any gene of interest, including the native coding sequence, can be operably linked to the regulatory elements of the invention and expressed in the developing floral tissue.

Exogenous products include plant enzymes and products as well as those from other sources including prokaryotes and other eukaryotes. Such products include enzymes, cofactors, hormones, and the like.

Reduction of the activity of specific genes (also known as gene silencing or gene suppression) is desirable for several aspects of genetic engineering in plants. The nucleotide sequence operably linked to a regulatory element disclosed herein can be an antisense sequence for a targeted gene. In this case, a desired phenotypic response is achieved by inhibiting production of the native protein encoded by a targeted gene. By "antisense sequence" is intended a DNA sequence that is in inverse orientation to the normal 5'-to-3' orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to, and capable of hybridizing with, the endogenous messenger RNA (mRNA) produced by transcription of the targeted gene. Thus the regulatory sequences disclosed herein can be operably linked to antisense DNA sequences to reduce or inhibit expression of a native protein in the developing flower or to regulate the development of the flower. See, for example, Sheehy et al. (1988) *Proc. Natl. Acad. Sci. USA* 85:8805-8809; and U.S. Pat. Nos. 5,107,065; 5,453,566; and 5,759,829. Downregulation of an endogenous gene may also be achieved through use of hairpin RNA (hpRNA) interference wherein the base-paired stem of the hairpin corresponds to a coding sequence to be silenced. See, for example, Mette et al. (2002) *EMBO J.* 19:5194-5201; Smith et al. (2000) *Nature* 407:319-320; WO 99/53050; WO 02/00904; WO 98/53083; Chuang and Meyerowitz (2000) *Proc. Natl. Acad. Sci. USA* 97:4985-4990; Stoutjesdijk et al. (2002) *Plant Physiol.* 129:1723-1731; Waterhouse and Helliwell (2003) *Nat. Rev. Genet.* 4:29-38;

The promoter sequence may also be of interest for use in transcriptional gene silencing (TGS). TGS is accomplished through use of hairpin RNA (hpRNA) constructs wherein the inverted repeat of the hairpin shares sequence identity with the promoter region of a gene to be silenced. Processing of the hpRNA into short RNAs which can interact with the homologous promoter region may trigger degradation or methylation to result in silencing. (Aufsatz, et al., (2002) *PNAS* 99 (Suppl. 4):16499-16506; Mette, et al., (2000) *EMBO J* 19(19):5194-5201)

Additional techniques for gene silencing are well known to one of skill in the art and include cosuppression (e.g., Taylor (1997) *Plant Cell* 9:1245; Jorgensen (1990) *Trends Biotech.* 8(12):340-344; Flavell (1994) *Proc. Natl. Acad. Sci. USA* 91:3490-3496; Finnegan et al. (1994) *Bio/Technology* 12:883-888; and Neuhuber et al. (1994) *Mol. Gen. Genet.* 244:230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *Proc. Natl. Acad. Sci. USA* 95:15502-15507), virus-induced gene silencing (Burton et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); ribozymes (Steinecke et al. (1992) *EMBO J.* 11:1525; and Perriman et al. (1993) *Antisense Res. Dev.* 3:253); oligonucleotide-mediated targeted modification (e.g., WO 03/076574 and WO 99/25853); Zn-finger targeted molecules (e.g., WO 01/52620; WO 03/048345; and WO 00/42219); transposon tagging (Maes et al. (1999) *Trends Plant Sci.* 4:90-96; Dharmapuri and Sonti (1999) *FEMS Microbiol. Lett.* 179:53-59; Meissner et al. (2000) *Plant J.* 22:265-274; Phogat et al. (2000) *J. Biosci.* 25:57-63; Walbot (2000) *Curr. Opin. Plant Biol.* 2:103-107; Gai et al. (2000) *Nucleic Acids Res.* 28:94-96; Fitzmaurice et al. (1999) *Genetics* 153:1919-1928; Bensen et al. (1995) *Plant Cell* 7:75-84; Mena et al. (1996) *Science* 274:1537-1540; and U.S. Pat. No. 5,962,764); each of which is herein incorporated by reference; and other methods or combinations of the above methods known to those of skill in the art.

The expression cassette may also include, at the 3' terminus of the isolated nucleotide sequence of interest, a transcriptional and translational termination region functional in plants. The termination region can be native with the promoter nucleotide sequence of the present invention, can be native with the DNA sequence of interest, or can be derived from another source.

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., 1989) *Nucleic Acids Res.* 17:7891-7903; Joshi, et al., (1987) *Nucleic Acid Res.* 15:9627-9639.

The expression cassettes can additionally contain 5' leader sequences. Such leader sequences can act to enhance translation. Translation leaders are known in the art and include: picornavirus leaders, for example: EMCV leader (Encephalomyocarditis 5' noncoding region), Elroy-Stein, et al., (1989) *Proc. Nat. Acad. Sci. USA* 86:6126-6130; potyvirus leaders, for example, TEV leader (Tobacco Etch Virus), Allison, et al., (1986); MDMV leader (Maize Dwarf Mosaic Virus), *Virology* 154:9-20; human immunoglobulin heavy-chain binding protein (BiP), Macejak, et al., (1991) *Nature* 353:90-94; untranslated leader from the coat protein mRNA of alfalfa mosaic virus (AMV RNA 4), Jobling, et al., (1987) *Nature* 325:622-625); tobacco mosaic virus leader (TMV), Gallie, et al., (1989) *Molecular Biology of RNA*, pages 237-256; and maize chlorotic mottle virus leader (MCMV) Lommel, et al., (1991) *Virology* 81:382-385. See also, Della-Cioppa, et al., (1987) *Plant Physiology* 84:965-968. The cassette can also contain sequences that enhance translation and/or mRNA stability such as introns.

In those instances where it is desirable to have the expressed product of the isolated nucleotide sequence directed to a particular organelle, particularly the plastid, amyloplast, or the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase, and the like.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions such as transitions and transversions, can be involved.

As noted herein, the present invention provides vectors capable of expressing genes of interest under the control of the regulatory elements. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook, et al. (supra).

The transformation vector, comprising a regulatory sequence of the present invention operably linked to an isolated nucleotide sequence in an expression cassette, can also contain at least one additional nucleotide sequence for a gene to be cotransformed into the organism. Alternatively, the additional sequence(s) can be provided on another transformation vector.

Vectors that are functional in plants can be binary plasmids derived from *Agrobacterium*. Such vectors are capable of transforming plant cells. These vectors contain left and right border sequences that are required for integration into the host (plant) chromosome. At a minimum, between these border sequences is the gene to be expressed under control of a regulatory element of the present invention. In one embodiment, a selectable marker and a reporter gene are also included. For ease of obtaining sufficient quantities of vector, a bacterial origin that allows replication in *E. coli* can be used.

Reporter genes can be included in the transformation vectors. Examples of suitable reporter genes known in the art can be found in, for example: Jefferson, et al., (1991) in *Plant Molecular Biology Manual*, ed. Gelvin, et al., (Kluwer Academic Publishers), pp. 1-33; DeWet, et al., (1987) *Mol. Cell. Biol.* 7:725-737; Goff, et al., (1990) *EMBO J.* 9:2517-2522; Kain et al. (1995) *BioTechniques* 19:650-655; and Chiu, et al., (1996) *Current Biology* 6:325-330.

Selectable marker genes for selection of transformed cells or tissues can be included in the transformation vectors. These can include genes that confer antibiotic resistance or resistance to herbicides. Examples of suitable selectable marker genes include, but are not limited to: genes encoding resistance to chloramphenicol, Herrera Estrella, et al., (1983) *EMBO J.* 2:987-992; methotrexate, Herrera Estrella, et al., (1983) *Nature* 303:209-213; Meijer, et al., (1991) *Plant Mol. Biol.* 16:807-820; hygromycin, Waldron, et al., (1985) *Plant Mol. Biol.* 5:103-108; Zhijian, et al., (1995) *Plant Science* 108:219-227; streptomycin, Jones, et al., (1987) *Mol. Gen.*

*Genet.* 210:86-91; spectinomycin, Bretagne-Sagnard, et al., (1996) *Transgenic Res.* 5:131-137; bleomycin, Hille, et al., (1990) *Plant Mol. Biol.* 7:171-176; sulfonamide, Guerineau, et al., (1990) *Plant Mol. Biol.* 15:127-136; bromoxynil, Stalker, et al., (1988) *Science* 242:419-423; glyphosate, Shaw, et al., (1986) *Science* 233:478481; phosphinothricin, DeBlock, et al., (1987) *EMBO J.* 6:2513-2518.

Other genes that could serve utility in the recovery of transgenic events but might not be required in the final product would include, but are not limited to: GUS (β-glucoronidase), Jefferson (1987) *Plant Mol. Biol. Rep.* 5:387); GFP (green florescence protein), Chalfie, et al., (1994) *Science* 263:802; luciferase, Teeri, et al., (1989) *EMBO J.* 8:343; and the maize genes encoding for anthocyanin production, Ludwig, et al., (1990) *Science* 247:449.

The transformation vector comprising a particular regulatory sequence of the present invention, operably linked to an isolated nucleotide sequence of interest in an expression cassette, can be used to transform any plant. In this manner, genetically modified plants, plant cells, plant tissue, seed, and the like can be obtained. Transformation protocols can vary depending on the type of plant or plant cell, e.g., monocot or dicot, targeted for transformation. Suitable methods of transforming plant cells include microinjection, Crossway, et al., (1986) *Biotechniques* 4:320-334; electroporation, Riggs, et al., (1986) *Proc. Natl. Acad. Sci.* USA 83:5602-5606; *Agrobacterium*-mediated transformation, see for example, Townsend, et al., U.S. Pat. No. 5,563,055; direct gene transfer, Paszkowski, et al., (1984) *EMBO J.* 3:2717-2722; and ballistic particle acceleration, see for example, Sanford, et al., U.S. Pat. Nos. 4,945,050, 5,036,006, 5,100,792, 5,371,015, and 5,478,744; Tomes, et al., (1995) in *Plant Cell, Tissue, and Organ Culture: Fundamental Methods*, ed. Gamborg and Phillips (Springer-Verlag, Berlin); and McCabe, et al., (1988) *Biotechnology* 6:923-926. Also see, Weissinger, et al., (1988) *Annual Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Datta, et al., (1990) *Biotechnology* 8:736-740 (rice); Klein, et al., (1988) *Proc. Natl. Acad. Sci.* USA 85:4305-4309 (maize); Klein, et al., (1988) *Biotechnology* 6:559-563 (maize); Klein, et al., (1988) *Plant Physiol.* 91:440-444 (maize); Fromm, et al., (1990) *Biotechnology* 8:833-839; Hooydaas-Van Slogteren, et al., (1984) *Nature* (London) 311:763-764; Bytebier, et al., (1987) *Proc. Natl. Acad. Sci.* USA 84:5345-5349 (Liliaceae); De Wet, et al., (1985) in *The Experimental Manipulation of Ovule Tissues*, ed. G. P. Chapman, et al., (Longman, N.Y.), pp. 197-209 (pollen); Kaeppler, et al., (1990) *Plant Cell Reports* 9:415-418; and Kaeppler, et al., (1992) *Theor. Appl. Genet.* 84:560-566 (whisker-mediated transformation); D. Halluin, et al., (1992) *Plant Cell* 4:1495-1505 (electroporation); Li, et al., (1993) *Plant Cell Reports* 12:250-255 and Christou, et al., (1995) *Annals of Botany* 75:407-413 (rice); Osjoda, et al., (1996) *Nature Biotechnology* 14:745-750 (maize via *Agrobacterium tumefaciens*); all of which are herein incorporated by reference.

The cells that have been transformed can be grown into plants in accordance with conventional ways. See, for example, McCormick, et al., (1986) *Plant Cell Reports* 5:81-84. These plants can then be grown and pollinated with the same transformed strain or different strains. A resulting plant having floral-meristem- or developing-flower-preferred expression of the desired phenotypic characteristic can then be identified. Two or more generations can be grown to ensure that expression of the desired phenotypic characteristic is stably maintained and inherited.

EXAMPLES

The following examples are offered by way of illustration and not by way of limitation.

Example 1

Isolation of Promoter Sequences Using Genome Walker

The promoter of SEQ ID NO: 1 was isolated following identification of the maize AP1-like coding sequence via proprietary EST p0127.cntav71r. Genomic DNA upstream of the coding sequence for maize AP1-like gene was isolated from maize inbred B73 using the Universal GenomeWalker™ Kit sold by CLONTECH (Palo Alto, Calif.), following the manufacturer's protocol. Gene-specific primers used in the Universal GenomeWalker™ system were:

PHN53489: CCCGCTCACTCTCGTCGCAGCAATG-GTGAT (SEQ ID NO: 6)

which was used with Clontech AP1 primer for the first round of PCR.

PHN53489: GAAAGATCAGGTGCCTCTCGAGTCTC-GACT (SEQ ID NO 7)

which was used with Clontech AP2 primer for the second round of PCR.

Example 2

Analysis of Expression of AP1-Like Gene

RNA was isolated from shoots of 4-week-old maize seedlings using the TriZol® method (Invitrogen, Carlsbad, Calif.). 15 µg total RNA was separated on 1% agarose MOPS-formaldehyde gels and blotted on Hybond™–N+ membrane (Amersham). The 1.2 kb full-length cDNA fragment from EST p0127.cntav71r was labeled using RediPrimeII™ kit (Amersham) and hybridized to membrane in ExpressHyb™ (CLONTECH, Palo Alto, Calif.) at 65° C. overnight. The membranes were washed twice in 2× SSC, 0.1% SDS at room temperature and twice in 0.× SSC, 0.1% SDS at 50° C. The membranes were autographed to visualize hybridization signals.

AP1-like gene expression in the shoots of maize and Tb1 mutant maize plants is depicted in FIG. 1 for, left to right, wild-type plant (W22), W22 plant introgressed with the teosinte 1L chromosome (T1L), W22 plant introgressed with the teosinte 1L and 3L chromosomes (T1L3L), Tb1/tb1-mum3 heterozygote (het) and tb1-mum3 homozygote (tb1). All are in W22 background.

Tb1 is a maize transcription factor which plays a major role in domestication of modern maize from the wild species teosinte. Maize differs from teosinte in its inflorescence structure; the maize tb1 mutant resembles teosinte. FIG. 1 shows that AP1-like gene expression is up-regulated in the tb1 mutant, consistent with its function in inflorescence meristem initiation and floral development.

Example 3

Vector Construction

Figure 2:
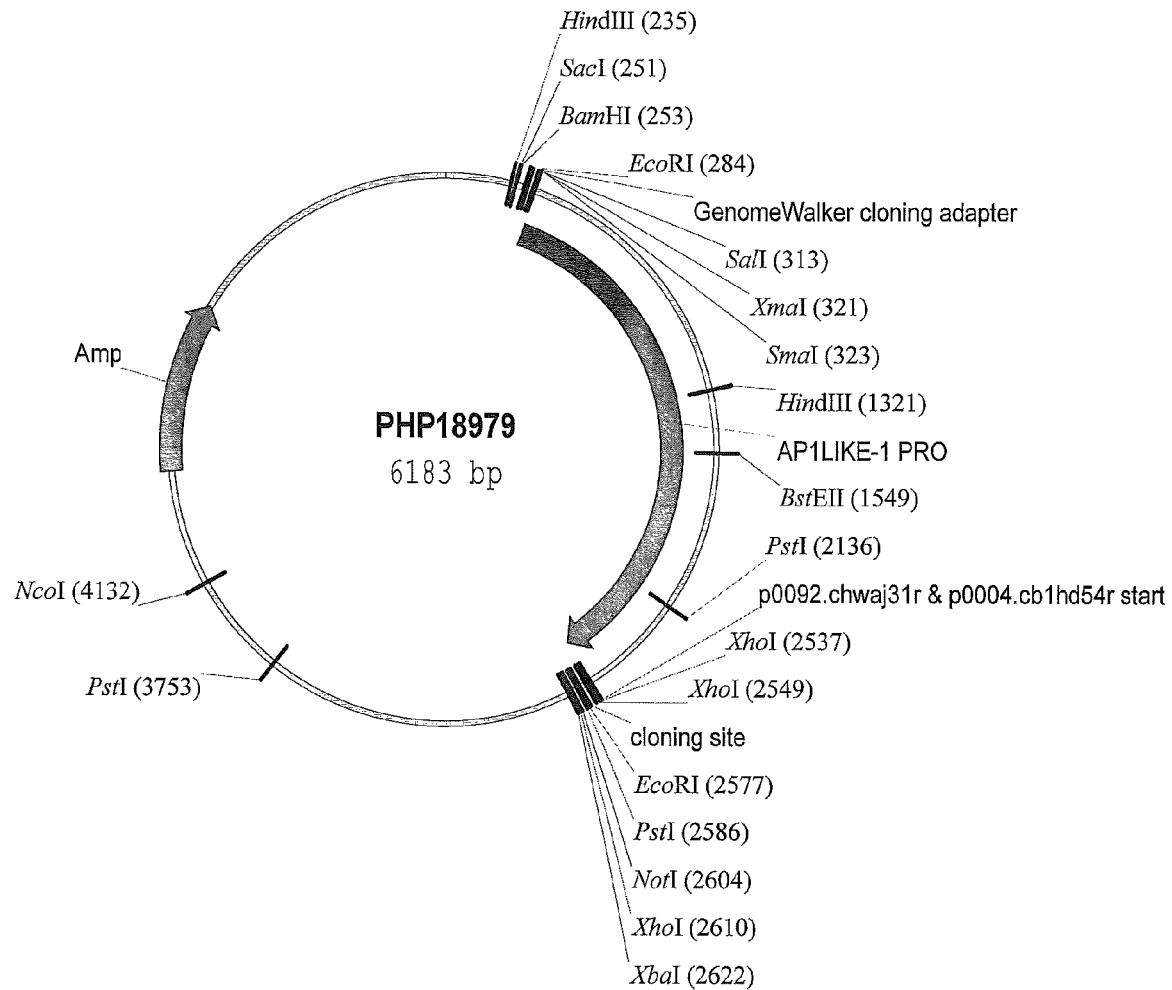
FIG. 2 is a diagram showing the PHP 18979 plasmid which comprises the AP1-like regulatory element of the invention.
Figure 4:
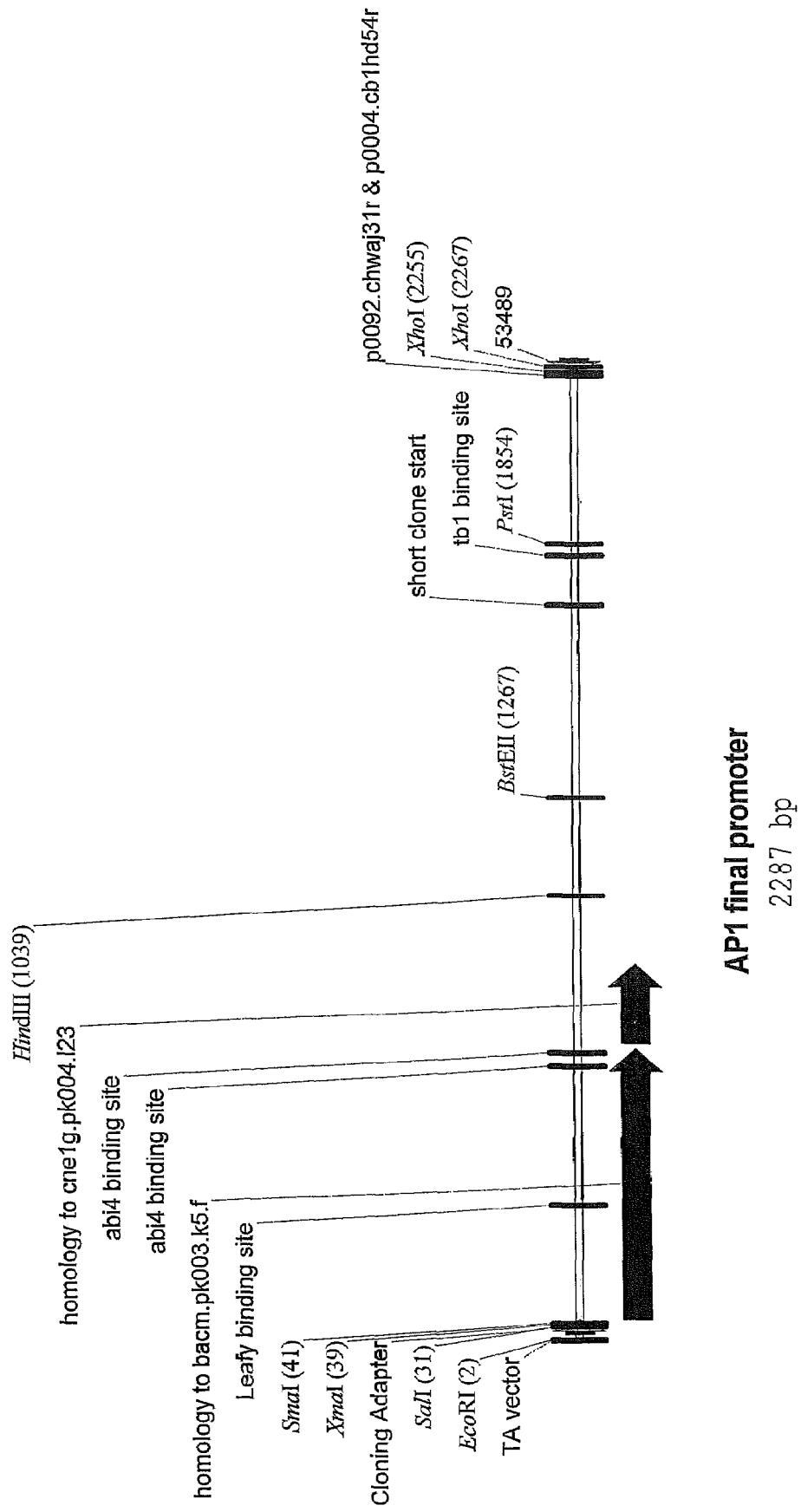
FIG. 4 is a diagram showing the AP1-like promoter sequence of the invention.
Figure 5A:
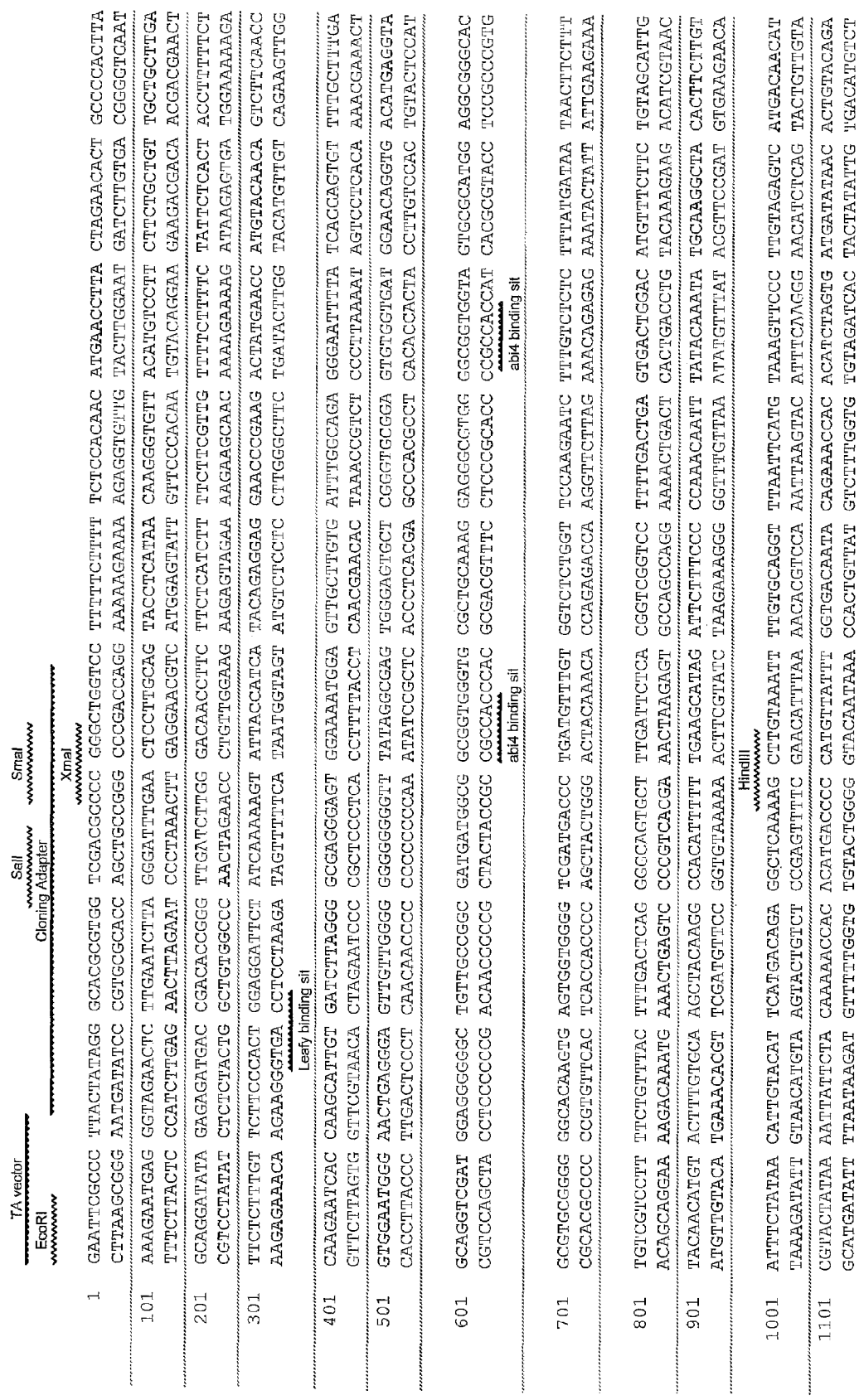
FIG. 5 is the sequence of the AP1-like promoter diagrammed in FIG. 4.

Using standard vector construction techniques known to those of skill in the art, a plasmid was prepared incorporating the AP1-like promoter of the invention (FIG. 2, FIG. 3, and SEQ ID NO: 2). Plasmid backbone was obtained from Japan

Example 4

Transgenics for AP1: IPT

Using standard protocols as set forth generally in Example 10, maize cells were transformed with an expression cassette comprising SEQ ID NO: 3 operably linked to an *Agrobacterium* IPT gene (see Akiyoshi et al. (1984) PNAS USA 81:5994-5998). SEQ ID NO: 3 is 1331 nucleotides in length and comprises nucleotides 990 through 2197 of SEQ ID NO: 1. The construct further included the ubiquitin promoter operably linked to the bar gene (Rathore, et al., (1993) *Plant Molecular Biology* 21:871-884). Plants were regenerated and transgene status determined based on herbicide resistance. Meristem tissue of T1 seedling plants was tested for expression of the transgene using RT-PCR (see, for example, Ausubel, et al., supra). Of nine transgene-positive plants, three exhibited expression of the operably-linked IPT, indicating that SEQ ID NO: 3 can effectively drive expression in the meristem tissue. As a control, seven transgene-negative plants were tested; none exhibited expression of IPT. These results confirm that SEQ ID NO: 3 represents a functional promoter.

Example 5

Transgenics for AP1: abi1

The *Arabidopsis* abi1 mutation disrupts abscisic acid signaling, resulting in a wilty phenotype under mild drought stress conditions. As reported by Leung, et al., (*Plant Cell* 9:759-771 (1997)), abi1 mutations affect both seeds and vegetative tissue, suggesting a signal transduction role for the ABI1 gene product upstream of tissue-specific cascades.

Using standard protocols as set forth generally in Example 10, maize cells were transformed with vector PHP22178, comprising SEQ ID NO: 4 operably linked to an *Arabidopsis* abi1 mutant gene (Meyer et al. (1994) *Science* 264:1452-1455). SEQ ID NO: 4 is 1547 nucleotides in length and is 99.9% identical to nucleotides 774 through 2197 of SEQ ID NO: 1. The construct further comprised the selectable markers DsRed2 (Living Colors®, CLONTECH, Palo Alto, Calif.) and MoPAT (maize-optimized phosphinothricin acetyl transferase) driven by the LTP2 (Kalla, et al., *Plant Journal* 6:849-860 (1994); U.S. Pat. No. 5,525,716) and ubiquitin promoters, respectively. Seedling T0 plants were grown in the greenhouse. At least ten transgenic events were transferred to the greenhouse and most did not survive, as the abi1 phenotype results in stunted growth and premature plant death. Non-transgenic control plants grew normally under the same conditions. These results confirm that SEQ ID NO: 4 represents a functional promoter.

Example 6

Transgenics for AP1: IAA-M

Using standard protocols as set forth generally in Example 10, maize cells are transformed with an expression cassette comprising SEQ ID NO: 5 operably linked to a nucleotide encoding the auxin biosynthetic gene IAA-M. SEQ ID NO: 5 is 1552 nucleotides in length and is 99.7% identical to nucleotides 770 through 2197 of SEQ ID NO: 1. Selectable marker MoPAT, driven by ubiquitin, is used to select transgenic tissues. Regenerated transgenic plants exhibiting maintenance of the auxin peak in the developing female inflorescence confirm promoter functionality of SEQ ID NO: 5. In maize, such targeted increases in auxin may positively affect ear growth and/or reduce kernel abortion under optimum or stress conditions.

Example 7

Confirmation of Tissue-Preferred Expression of ZmAP1-Like Gene

MPSS™ analysis (Solexa, Inc.; formerly Lynx Therapeutics; see, *Nature Biotechnology* 18:630-634 (2000)) was performed to analyze expression of the endogenous ZAP coding sequence. FIG. 6 shows the high relative level of ZAP expression in the immature ear tissues of maize.

Example 8

Creation and Testing of Variant Promoter Sequences

One or more of the disclosed promoter sequences (SEQ ID NOS: 1, 3, 4, and 5) is modified, for example by using an exonuclease to generate a series of deletions from the 5' and/or 3' ends. Other means of creating fragments or variants include, but are not limited to, point mutation and rearrangement or "shuffling." Strategies for such DNA shuffling are known in the art. See, for example, Stemmer (1995) *Proc. Natl. Acad. Sci. USA* 91:10757-10751; Stemmer (1995) *Nature* 370:389-391; Crameri, et al., (1997) *Nature Biotech.* 15:536-538; Moore, et al., (1997) *J. Mol. Biol.* 272:336-357; Zhang, et al., (1997) *Proc. Natl. Acad. Sci. USA* 95:5505-5509; Crameri, et al., (1998) *Nature* 391:288-291; and U.S. Pat. No. 5,605,793. Specific motifs identified within the promoter region may be altered as to size, number, orientation, and/or sequence. A candidate promoter fragment or variant which results from any such modification is linked to a coding sequence in an expression cassette. The coding sequence may encode a marker polypeptide as described elsewhere herein. Cells are transformed with the expression cassette as described elsewhere herein and screened for expression of the operably-linked coding sequence, to test functionality of the promoter fragment or variant. Fragments or variants may be tested in combination with enhancers or intron sequences. Cells may be screened for expression at any one or more of various developmental stages, including callus tissue, seedling, mature plant, or seed.

Example 9

Biolistic Transformation

A plasmid is prepared as described elsewhere herein and used to bombard immature maize embryos from donor plants, as follows. Media recipes also follow below.

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 5 hours and then aligned within the 2.5 cm target zone in preparation for bombardment.

A plasmid vector comprising the ZAP promoter sequence operably linked to a gene of interest is made. The plasmid may further comprise a selectable marker gene under control of appropriate regulatory sequences; alternatively, a selectable marker may be provided on a separate plasmid. Plasmid DNA is precipitated onto 1.1 µm (average diameter) tungsten pellets using a $CaCl_2$ precipitation procedure as follows: 100 µl prepared tungsten particles in water; 10 µl (1 µg) DNA in Tris EDTA buffer (1 µg total DNA); 100 µl 2.5 M $CaCl_2$; and, 10 µl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

The sample plates are bombarded at level #5 in particle gun #HE35-1 or #HE35-2. All samples receive a single shot at 650 PSI, with a total of ten aliquots taken from each tube of prepared particles/DNA.

Following bombardment, the embryos are kept on non-selective medium for 2 days, then transferred to selection medium and subcultured every 2 weeks. After approximately 10 weeks of selection, selection-resistant callus clones are transferred to 288J medium to initiate plant regeneration. Following somatic embryo maturation (2-5 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored under various conditions and compared to control plants. Regenerated plants are the T1 generation; next-generation progeny are T1, then T2, etc.

Bombardment medium (560Y) comprises 5.0 g/l N6 basal salts (SIGMA C-1516), 1.0 ml/l Eriksson's Vitamin Mix (1000× SIGMA-1511), 0.5 mg/l thiamine HCl, 120.0 g/l sucrose, 1.0 mg/l 2,5-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) may comprise 5.0 g/l N6 basal salts (SIGMA C-1516), 1.0 ml/l Eriksson's Vitamin Mix (1000× SIGMA-1511), 0.5 mg/l thiamine HCl, 30.0 g/l sucrose, and 2.0 mg/l 2,5-D (brought to volume with D-I $H_2O$ following adjustment to pH 5.8 with KOH); 3.0 g/l Gelrite (added after bringing to volume with D-I $H_2O$); and 0.85 mg/l silver nitrate and a selection agent, for example, 3.0 mg/l bialaphos (both added after sterilizing the medium and cooling to room temperature).

Plant regeneration medium (288J) comprises 5.3 g/l MS salts (GIBCO 11117-075), 5.0 ml/l MS vitamins stock solution (0.100 g nicotinic acid, 0.02 g/l thiamine HCL, 0.10 g/l pyridoxine HCL, and 0.50 g/l glycine brought to volume with polished D-I $H_2O$) (Murashige and Skoog (1962) *Physiol. Plant.* 15:573), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 5.3 g/l MS salts (GIBCO 11117-075), 5.0 ml/l MS vitamins stock solution (0.100 g/l nicotinic acid, 0.02 g/l thiamine HCL, 0.10 g/l pyridoxine HCL, and 0.50 g/l glycine brought to volume with polished D-I $H_2O$), 0.1 g/l myo-inositol, and 50.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 10

*Agrobacterium* Transformation

For *Agrobacterium*-mediated transformation of maize, the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the RR6 nucleotide sequence to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 5: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants. Regenerated plants are the T0 generation; next-generation progeny are T1, then T2, etc.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

What is claimed is:

1. An isolated nucleic acid comprising a functional regulatory element represented by a sequence selected from the group consisting of:
   (a) SEQ ID NO: 1;
   (b) SEQ ID NO: 3;
   (c) SEQ ID NO: 4;
   (d) SEQ ID NO: 5; and
   (e) a fragment of SEQ ID NO: 1 comprising nucleotides 990-2197.

2. An expression cassette comprising a first nucleotide sequence which is a regulatory element, and a second nucleotide sequence operably linked to the regulatory element, wherein the regulatory element is represented by a sequence selected from the group consisting of:
   (a) SEQ ID NO: 1;
   (b) SEQ ID NO: 3;
   (c) SEQ ID NO: 4;
   (d) SEQ ID NO: 5; and
   (e) a fragment of SEQ ID NO: 1 comprising nucleotides 990-2197.

3. A transformation vector comprising the expression cassette of claim 2.

4. A plant stably transformed with the expression cassette of claim 2.

5. The plant of claim 4, wherein said plant is a monocot.

6. The plant of claim 5, wherein said monocot is maize, wheat, rice, barley, sorghum, or rye.

7. Seed of the plant of claim 4, wherein said seed comprise the expression cassette of claim 2.

8. A method for selectively expressing a nucleotide sequence in a plant cell, the method comprising transforming a plant cell with a transformation vector comprising an expression cassette, said expression cassette comprising a first nucleotide sequence which is a regulatory element and a second nucleotide sequence operably linked to the regulatory element, wherein the regulatory element is represented by a sequence selected from the group consisting of:
   (a) SEQ ID NO: 1;
   (b) SEQ ID NO: 3;
   (c) SEQ ID NO: 4;
   (d) SEQ ID NO: 5; and
   (e) a fragment of SEQ ID NO: 1 comprising nucleotides 990-2197.

9. The method of claim 8 wherein the plant cell is comprised by callus tissue.

10. The method of claim 8 further comprising regenerating a stably transformed plant from said transformed plant cell.

11. A stably transformed plant created by the method of claim 10.

12. The plant of claim 11 wherein the phenotype of said stably transformed plant is altered relative to a nontransgenic isoline.

13. The plant of claim 12 wherein the phenotype of one or more reproductive structures is altered relative to a nontransgenic isoline.

14. The method of claim 8, wherein said second nucleotide sequence encodes a gene involved in fatty acid synthesis.

15. A plant cell stably transformed with an expression cassette comprising a first nucleotide sequence which is a regulatory element and a second nucleotide sequence operably linked to the regulatory element, wherein the regulatory element is represented by a sequence selected from the group consisting of:

(a) SEQ ID NO: 1;
(b) SEQ ID NO: 3;
(c) SEQ ID NO: 4;
(d) SEQ ID NO: 5; and
(e) a fragment of SEQ ID NO: 1 comprising nucleotides 990-2197.

16. The plant cell of claim 15, wherein said plant cell is from a monocot.

17. The plant cell of claim 16, wherein said plant cell is from maize, wheat, rice, barley, sorghum, or rye.

* * * * *